United States Patent
Glucksmann et al.

(10) Patent No.: US 6,500,657 B1
(45) Date of Patent: Dec. 31, 2002

(54) 33167, A NOVEL HUMAN HYDROLASE AND USES THEREFOR

(75) Inventors: Maria Alexandra Glucksmann, Lexington; Rachel Meyers, Newton; Mark Williamson, Saugus, all of MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/584,568

(22) Filed: May 31, 2000

Related U.S. Application Data

(60) Provisional application No. 60/193,954, filed on Mar. 31, 2000.

(51) Int. Cl.[7] .............................. C12N 9/14; C12N 15/55
(52) U.S. Cl. ........................ 435/195; 435/6; 435/252.3; 435/325; 435/320.1; 536/23.2
(58) Field of Search ........................... 435/320.1, 252.3, 435/325, 195, 6, 975; 536/23.2

(56) References Cited

FOREIGN PATENT DOCUMENTS

| WO | WO 99/52675 | 10/1999 |
|---|---|---|
| WO | WO 99/58675 | * 11/1999 |

OTHER PUBLICATIONS

Hillier, L., et al., Accession No. AA410674 (1990).*
Accession No. AA568168 (1997).*
Hillier, L. et al. , Accession No. AA464030 (1997).*
Hillier, L., et al., Accession No. AA434281 (1997).*
Adams, Mark D. et al. "The Genome Sequence of *Drosophila melanogaster*" *Science* 287:2185 (Mar. 24, 2000).
Benhamou, Simone et al. "Association between Lung Cancer and Microsomal Epoxide Hydrolase Genotypes" *Cancer Res.* 58(23):5291–93 (1998).
Blattner, Frederick R. et al. "The Complete Genome Sequence of *Escherichia coli* K–12" *Science* 277(5331):1453–74 (1997).
The C. elegans Sequencing Consortium "Genome Sequence of the Nematode C. elegans: A Platform for Investigating Biology" *Science* 282(5396):2012–18 (Dec. 11, 1998).
Derewenda, Zygmunt S. and Derewenda, Urszula "Relationships among serine phydrolase: evidence for a common structural motif in triacylglyceride lipases and esterases" *Biochem. Cell. Biol.*69:842–51 (1991).
Fleischmann, Robert D. et al. "Whole–Genome Random Sequencing and Assembly of *Haemophilus influenzae* Rd" *Science* 269(5223):496–512 (1995).
Fountoulakis, Michael et al. "Enrichment of low abundance proteins of *Escherichia cola* by hydroxyapatite chromatography" *Electrophoresis* 20(11):2181–95 (1999).

Krejci, Eric et al. "Cholinesterase–like domains in enzymes and structual proteins: Functional and evolutionary relationships and identification of a catalytically essential aspartic acid" *Proc. Natl. Acad. Sci.* USA 88:6647–51 (1991).
London, Stephanie J. et al. "Lung cancer risk in relation to genetic polymorphisms of microsomal epoxide hydrolase among African–Americans and Caucasians in Los Angeles County" *Lung Cancer* 28(2):147–55 (2000).
Ollis, David L. et al. "the $\alpha/\beta$ hydrolasefold" *Protein Engineering* 5(3):197:211 (1992).
Oshima, Taku et al. "A 718–kb DNA Sequence of the *Escherichia coli* K–12 Genome Corresponding to the 12.7–28.0 min Region on the Linkage Map" *DNA Res.* 3(3):137–55 (1996).
Rieger, Michael et al. "Sequence Analysis of 203 Kilobases from *Saccharomyces cerevisiae* Chromosome VII" *Yeast* 13:1077–90 (1997).
Schrag, Joseph D. and Cygler, Miroslaw "Lipases and $\alpha/\beta$ Hydrolase Fold" *Enzymol.* 284:85–107 (1997).
Genbank Accession No. AAF46249 for CG2059 gene product [Drosophila melanogaster] (2000).
Genbank Accession No. AAF54685 got CG14717 gene product [Drosophila melanogaster] (2000).
Genbank Accession No. CAA22555 for hypothetical alpha/beta hydrolase fold domain protein [Schizosaccharomyces pombe] (2000).
Genbank Accession No. CAB03219 for similar to alpha/beta hydrolase fold~cDNA EST EMBL:T02320 comes from the gene [Caenorhabditis elegans] (1996).
Genbank Accession No. CAB04232 predicted using Genefinder~similar to alpha/beta hydrolase fold [Caenorhabditis elegans] (1998).
Genbank Accession No. P53219 for hypothetical 38.5 KDA protein in ERV1–GLS2 Intergenic region (1996).
Genbank Accession No. P75736 for Putuative Esterase/Lipase YBFF (1997).
Genbank Accession No. Q57427 Putative Esterase/Lipase Hl0193 (1997).

* cited by examiner

Primary Examiner—Charles L. Patterson, Jr.
(74) Attorney, Agent, or Firm—Lahive & Cockfield, LLP; Amy E. Mandragouras; Maria C. Laccotripe

(57) ABSTRACT

The invention provides isolated nucleic acids molecules, designated HYDL-1 nucleic acid molecules, which encode novel hydrolase molecules. The invention also provides antisense nucleic acid molecules, recombinant expression vectors containing HYDL-1 nucleic acid molecules, host cells into which the expression vectors have been introduced, and nonhuman transgenic animals in which an HYDL-1 gene has been introduced or disrupted. The invention still further provides isolated HYDL-1 proteins, fusion proteins, antigenic peptides and anti-HYDL-1 antibodies. Diagnostic methods utilizing compositions of the invention are also provided.

12 Claims, 12 Drawing Sheets

```
cgagctaggg cgggagaagg agcgcgggga ggacgtacct tgtggg atg cga gcc    55
                                                    Met Arg Ala
                                                     1 ggc caa cag ctt gca agc atg ctc cgc tgg acc cga gcc tgg agg ctc   103
Gly Gln Gln Leu Ala Ser Met Leu Arg Trp Thr Arg Ala Trp Arg Leu
     5               10                  15 ccg cgt gag gga ctc ggc ccc cac ggc cct agc ttc gcg agg gtg cct   151
Pro Arg Glu Gly Leu Gly Pro His Gly Pro Ser Phe Ala Arg Val Pro
 20              25                  30                      35 gtc gca ccc agc agc agc agc ggc ggc cga ggg ggc gcc gag ccg agg   199
Val Ala Pro Ser Ser Ser Ser Gly Gly Arg Gly Gly Ala Glu Pro Arg
             40                  45                      50 ccg ctt ccg ctt tcc tac agg ctt ctg gac ggg gag gca gcc ctc ccg   247
Pro Leu Pro Leu Ser Tyr Arg Leu Leu Asp Gly Glu Ala Ala Leu Pro
                 55                  60                  65 gcc gtc gtc ttt ttg cac ggg ctc ttc ggc agc aaa act aac ttc aac   295
Ala Val Val Phe Leu His Gly Leu Phe Gly Ser Lys Thr Asn Phe Asn
             70                  75                  80 tcc atc gcc aag atc ttg gcc cag cag aca ggc cgt agg gtg ctg acg   343
Ser Ile Ala Lys Ile Leu Ala Gln Gln Thr Gly Arg Arg Val Leu Thr
         85                  90                  95 gtg gat gct cgt aac cac ggt gac agc ccc cac agc cca gac atg agc   391
Val Asp Ala Arg Asn His Gly Asp Ser Pro His Ser Pro Asp Met Ser
100             105                 110                 115 tac gag atc atg agc cag gac ctg cag gac ctt ctg ccc cag ctg ggc   439
Tyr Glu Ile Met Ser Gln Asp Leu Gln Asp Leu Leu Pro Gln Leu Gly
                120                 125                 130 ctg gtg ccc tgc gtc gtc gtt ggc cac agc atg gga gga aag aca gcc   487
Leu Val Pro Cys Val Val Val Gly His Ser Met Gly Gly Lys Thr Ala
            135                 140                 145 atg ctg ctg gca cta cag agg cca gag ctg gtg gaa cgt ctc att gct   535
Met Leu Leu Ala Leu Gln Arg Pro Glu Leu Val Glu Arg Leu Ile Ala
        150                 155                 160 gta gat atc agc cca gtg gaa agc aca ggt gtc tcc cac ttt gca acc   583
Val Asp Ile Ser Pro Val Glu Ser Thr Gly Val Ser His Phe Ala Thr
165                 170                 175 tat gtg gca gcc atg agg gcc atc aac atc gca gat gag ctg ccc cgc   631
Tyr Val Ala Ala Met Arg Ala Ile Asn Ile Ala Asp Glu Leu Pro Arg
180                 185                 190                 195 tcc cgt gcc cga aaa ctg gcg gat gaa cag ctc agt tct gtc atc cag   679
Ser Arg Ala Arg Lys Leu Ala Asp Glu Gln Leu Ser Ser Val Ile Gln
                200                 205                 210
```

Fig. 1

```
gac atg gcc gtg cgg cag cac ctg ctc act aac ctg gta gag gta gac   727
Asp Met Ala Val Arg Gln His Leu Leu Thr Asn Leu Val Glu Val Asp
        215                 220                 225 ggg cgc ttc gtg tgg agg gtg aac ttg gat gcc ctg acc cag cac cta   775
Gly Arg Phe Val Trp Arg Val Asn Leu Asp Ala Leu Thr Gln His Leu
        230                 235                 240 gac aag atc ttg gct ttc cca cag agg cag gag tcc tac ctc ggg cca   823
Asp Lys Ile Leu Ala Phe Pro Gln Arg Gln Glu Ser Tyr Leu Gly Pro
        245                 250                 255 aca ctc ttt ctc ctt ggt gga aac tcc cag ttc gtg cat ccc agc cac   871
Thr Leu Phe Leu Leu Gly Gly Asn Ser Gln Phe Val His Pro Ser His
260                 265                 270                 275 cac cct gag att atg cgg ctc ttc cct cgg gcc cag atg cag acg gtg   919
His Pro Glu Ile Met Arg Leu Phe Pro Arg Ala Gln Met Gln Thr Val
                280                 285                 290 ccg aac gct ggc cac tgg atc cac gct gac cgc cca cag gac ttc ata   967
Pro Asn Ala Gly His Trp Ile His Ala Asp Arg Pro Gln Asp Phe Ile
                295                 300                 305 gct gcc atc cga ggc ttc ctg gtc taagagttgc tggcaagaag atggccgggc  1021
Ala Ala Ile Arg Gly Phe Leu Val
            310             315 gtggtggctc atgcctgtaa ttccagcact ttgggaggct aaggcgggag gatgacttga  1081
ggccaggagt tggagaccag cctggccaac atggtgaaac cctgtctcta ctaaaaatac  1141
aaaaattagc ctggcgtggt ggtgcacacc tgtaatccca gctactctgg aggctgaggc  1201
aggagaatca cttgaaccct ggaggcagag gttgcaatga gccgagatca caccactaca  1261
ctccagccta ggcaacagag caagactctg tctcaaaaaa aaaaaaaaaa aaaaaaaaa   1321 aggggccgta g                                                      1332
```

Fig. 1
Continued

Transmembrane Segments Predicted by MEMSAT

| Start | End | Orient | Score |
|---|---|---|---|
| 130 | 152 | out-->ins | 0.9 |
| 255 | 271 | ins-->out | 0.4 |

>33167
MRAGQQLASMLRWTRAWRLPREGLGPHGPSFARVPVAPSSSSGGRGGAEPRPLPLSYRLL
DGEAALPAVVFLHGLFGSKTNFNSIAKILAQQTGRRVLTVDARNHGDSPHSPDMSYEIMS
QDLQDLLPQPGLVPCVVVGHSMGGKTAMLLALQRPELVERLIAVDISPVESTGVSHFATY
VAAMRAINIADELPRSRARKLADEQLSSVIQDMAVRQHLLTNLVEVDGRFVWRVNLDALT
QHLDKILAFPQRQESYLGPTLFLLGGNSQFVHPSHHPEIMRLFPRAQMQTVPNAGHWIHA
DRPQDFIAAIRGFLV

Fig. 3

```
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - -
HMM file:              /prod/ddm/seqanal/PFAM/pfam5.0/Pfam
Sequence file:         /prod/ddm/wspace/orfanal/oa-script.6123.seq
- - - - - - - - - - - - - - - - - - - - - - - - - - - - - - - - - - -
Query:  33167

Scores for sequence family classification (score includes all domains):
Model           Description                                Score      E-value  N
--------        -----------                                -----      -------  ---
abhydrolase     alpha/beta hydrolase fold                   83.1      5.6e-21  1
Thioesterase    Thioesterase domain                        -33.6         0.48  1
Lipase_3        Lipase                                     -73.3          4.9  1

Parsed for domains:

Model           Domain   seq-f  seq-t   hmm-f  hmm-t       score   E-value
--------        ------   -----  -----   -----  -----       -----   -------
Lipase_3        1/1        75    247 ..     1    224 []    -73.3       4.9
Thioesterase    1/1        67    287 ..     1    267 []    -33.6      0.48
abhydrolase     1/1        95    314 ..     1    233 []     83.1   5.6e-21

Alignments of top-scoring domains:
Lipase_3: domain 1 of 1, from 75 to 247: score -73.3, E = 4.9
                  *->FRGTntglqwiaellfglveytffdfvdggkvhagFldaYldvwndg
                     G+ t ++ ia+ l+++++         +v     +++ d  +++
        33167  75     LFGSKTNFNSIAKILAQQTGR---------RVLTVDARNHGDSPHSP  112 kfakksARDq....iedevqdlveayPdEdYsvtVTGHSLGGAlAtLaAl
                     D++ + +  +++qdl+++ +       ++V+GHS GG  A L Al
        33167  113 --------DMsyeiMSQDLQDLLPQLGL--VPCVVVGHSMGGKTAMLLAL  152 d...laknglnvpksKiqvklytyGqPRVGdkaFAklhtneqgpnsyRvv
                   +++l+++ + v+ s  +v          +G    FA ++        ++R +
        33167  153 QrpeLVERLIAVDIS--PVE-------STGVSHFATYVA------AMRAI  187 hnrDiVPhlPplaeqdnfgyyHhstEiWydddmskglklkanykvCtghd
                   +  D  P+  +++  +d +         +      dm      +  + +t+
        33167  188 NIADELPRSRARKLADEQ------LSSVIQDMA------VRQHLLTN--  222 lesedhgvdvfCSngivsrgfiltsiedHlhYFg<-*
                  l++  d         + v+r+ +++ +  H1+
        33167  223 LVEVD--------GRFVWRVNLDALTQ-HLDKIL       247
```

Fig. 4

```
Thioesterase: domain 1 of 1, from 67 to 287: score -33.6, E = 0.48
                   *->rpLfcfPpAgGgsasyfrnlaralpgt.lvevsavqlPgredRrgEp
                      + ++ ++   G s  + f+++a+ 1+ +++  v++v ++ ++d
      33167    67     PAVVFLHGLFG-SKTNFNSIAKILAQQtGRRVLTVDARNHGDS---- 108 lltsieelaeeyaealraiqpeGdivPYaLfGhSmGGllAfEvArrLerr
                      ++s +   e + + 1++++p    vP +++GhSmGG  A+ +A  L+r
      33167   109     -PHSPDMSYEIMSQDLQDLLPQLGLVPCVVVGHSMGGKTAMLLA--LQRP 155 qdgGeevsgLilsDayaPytt.erreashllgddetgnaleeaesvsqal
                         e v++Li +D+++    t++++ a++ +++++++
      33167   156     ----ELVERLIAVDISPVESTgVSHFATYVAAMRAIN-----------I 189 laelrrlggtkppelledeellslaLpalradyraletyr..avpieaps
                      +el r +         1+de+1 s + ++ +  + ++   + + + +++
      33167   190     ADELPRSRAR----KLADEQLSSVIQDMAVRQHLLTNLVEvdGRFVWRV- 234 vratlfygaddplatldgllaadrtkaygevgedrWreytpgafdvrmlp
                      ++ +++ + d++ + +                      +++ ++   +++1
      33167   235     -NLDALTQHLDKILAFP-------------------QRQESYLGPTLFLL 264

GdHFylle.dhveleevlehilral<-*
                      G++    ++++h   +e+++   ra
      33167   265     GGNSQFVHpSH--HPEIMRLFPRAQ     287 abhydrolase: domain 1 of 1, from 95 to 314: score 83.1, E = 5.6e-21
                   *->frvialDlrGfGeSsrpsdladyrfddlaedleaIIdalgldkpvil
                      +rv++ D r++G S+   +d +++ ++ dl+ 11 +lgl +  ++
      33167    95     RRVLTVDARNHGDSP---HSPDMSYEIMSQDLQDLLPQLGLVP-CVV 137 vGhSmGGalaaayaakyPeervkalvlvstpapaglssrlfprlgnlegl
                      vGhSmGG +a  +a++ Pe +v +l++v+   + s+ +  ++   +
      33167   138     VGHSMGGKTAMLLALQRPE-LVERLIAVDI--SPVESTGVSH-FATYVAA 183 llanffnrlsrsveallgralkqffllgrpfvsdflkqaedwlsslarpg
                      + a++ + +  +++ +++++a++q+ ++ +++  ++ +  +  1    +
      33167   184     MRAINIA-DELPRSRARKLADEQLSSVIQDMANRQHLLTN--LVEVDG-- 228 etdggdgllgyavalgkllqwdrs.alkdikvPtlviwgddDplvplkas
                      ++  +1+      +  +++  +++++  ++ Ptl + g++ ++v + ++
      33167   229     RFVWRVNLDA--LTQHLDKILAFPqRQESYLGPTLFLLGGNSQFVHPSHH 276 eklsalfpnaevvviddagHlallekpeevaeli.kfl<-*
                      + + +lfp+a+   +++agH+++ ++p+++  +i+ fl
      33167   277     PEIMRLFPRAQMQTVPNAGHWIHADRPQDFIAAIrGFL      314
```

Fig. 4
continued

```
CLUSTAL W (1.74) multiple sequence alignment
Q57427           ----------MIFIF--ISLFAKIFFNYNDF--FTNSHVKIMAKSLLNY-----------
P75736           ------------------------------------MKLNIRAQTAQN-----------
Fbh33167F111     -MRAGQQLASMLRWTRAWRLPREGLGPHGPS--FARVPVAPSSSSGGRGG-------AEP
3878848          -----MLVSRNLAKTISNSKNAKNIHTSCRK--FAPVPMTYASYSSPE-----------
3876571          --------------MNSKLLNLARRFPHSDS--TSSMMLANLTFGNMR-----------
7290805          MQRLTKSLRSLPFPAGKILRTQLVVRREYSS--EIPDPVELSFDSYTGE-----------
4049528          -----------------------------MS--LKPVKLAFEKYSATV-----------
P53219           --MMILGKAGILAQYGTIYVRQNTIRNNLSSCIFKQSLCAFHSLAKVLQQKQVPLDLSYD
7299497          -------MARQRLLGSILSKGGAQVLRNFQS-FVQGTRLEYVSYTSPR-----------

Q57427           ----QFHQVKQ-TINTPVLIFIHGLFGDMDNLGVIARAFSEHYS--ILRIDLRNHGHSFH
P75736           -----QHN------NSP-IVLVHGLFGSLDNLGVLARDLVNDHN--IIQVDMRNHGLSPR
Fbh33167F111     RPLPLSYRLLDGEAALPAVVFLHGLFGSKTNFNSIAKILAQQTGRRVLTVDARNHGDSPH
3878848          -----LDR------NSP-LVIVHGLFGQKQNWWNSVGKALHKKLEAPVYAVDVRNHGSSPH
3876571          -----S-K------GTP-LILVPGLFGTKENWIQVGKDLSQRLGCMVFAVENRNHGSFSK
7290805          -----NPE------TSPPLLTYHGLFGSKQNWRGISKALVRKVSRKVYAIDVRNHGESPH
4049528          ------AK------HPP-VLIFHGLLGSKRNWRSLAKKFSCKLDRDIYAIDQRCHGDSPC
P53219           IIKRDAVKTGDEGKPRPPIIILHGLFGNKLNNRSIGRNLNKKLGRDVYLLDLRNHGSSPH
7299497          -------NQ-----MQAPPIVVMHDLNLSLESWRQVAVNLSQVGLRQVITVDARNHGLSPY
                        .   *  ::   .*      .   :.   :        :  ::  *  **

Q57427           SEKMNYQLMAEDVIAVIR----HLNLSKVILIGHSMGGKTAMKITALC---PELVEKLIVI
P75736           DPVMNYPAMAQDLVDTLD----AQQIDKATFIGHSMGGKAVMALTALA---SDRIDKLVAI
Fbh33167F111     SPDMSYEIMSQDLQDLLP----QLGLVPCVVVGHSMGGKTAMLLALQR---PELVERLIAV
3878848          TETMSYTEMAEDLVLFIDKVKEETKKTRVNLLGHSMGGKIVMRLAIDSKWSDRIEKLIVE
3876571          AASMTYEEMADDLVGFIDWVRKITGEDKVNLHGHSMGGKAVTQLATTPEYSSRIKSLIVE
7290805          SSVHNSKAMSEDLRLFME----QRSHPNAACMGHSMGGRSMMYFARKY---PELVERLIVV
4049528          VAPLSYSAMALDAFQFMK----DHKLDKASIIGHSMGAKTAMVTALKW---PDKVEKLVVV
P53219           SSVHNYEVMSEDVKHFIT-KHELNTNGGPIIIGHSMGGKVAMMLVLKN---PQLCSMLVCI
7299497          ITGHSPMHLAADVEALMS----HQRLNKIVALGHGMGGRAMMTLALTQ---PQLVERVILV
                  ::   *    :         **.**.:         ..  .::

Q57427           DMSPMPYEG-FGH-KDVFNGLFAVKNAKP---ENRQQAKPILKQEIN----DEDVVQFML
P75736           DIAPVDYHV-RRH-DEIFAAINAVSESDA---QTRQQAAAIMRQHLN----EEGVIQFLL
Fbh33167F111     DISPVESTG-VSHFATYVAAMRAINIADE---LPRSRARKLADEQLSSVIQDMAVRQHLL
3878848          DVSPKGYS--RRH-LEFRELIKTMRNVDLC--RTRKEILKDLESAIP----DLAMRQFIL
3876571          DMSPLGYP--LKR-AEYLECIKQMIATDMN--KSRSEVMAELGEKVS----KVLLYQFVR
7290805          DISPIVPRSTGEMTEIFDAMVSLDLSPS----MSMSEGRKIAREKLLKAT-EDETVDFIM
4049528          DNSPWYQDLPRDY-GAYFRKMIQIDEANI---TKYSEADKMMSTVEK----DILVRSFLL
P53219           ENAPVSLRP-NAEFVEYIKALMEIVNDKGKTIRTLKQADEHLAERIGG---NELVRRFLL
7299497          DITPAPVPSNFYLTRQVFEMMLQVAPSIPSN-LSLSEGRTFILPLFQDVVHDASELRRII
                 : :*                 :  :                         .      :

Q57427           KSFDVNS---A--------DCFRFNLTALFNNYAN--IMDW----EKVRVFT-PTLFIKGG
P75736           KSFVDG-----------EWRFNVPVLWDQYPH--IVGW----EKIPAWDHPALFIPGG
Fbh33167F111     TNLVEVD---GR------FVWRVNLDALTQHLDK--ILAFP---QRQESYLGPTLFLLGG
3878848          TNLQPSSENEGQ------MEWKININTIDSHVDE--ILGYT---LPVGSFRGPTLFLHGA
3876571          GNLGEDVN--GK------AHWICNLNVIDETYIY--LLSHD---IRFGVFDGPTLFQRAP
7290805          LNLRKNPD-TGA------FSWACNAHVLREFLTR--FDKYQSNLEELPPYTGPTTFICGT
4049528          SNLKKDSNNSNT------FKFRVPIELISKSLKT--IEGFPAS-LNDLVYDSPTLVIRAL
P53219           TALKKVKMDNSSSVSSYTFEERIPLATLKDAIVKGEIAAWP--LDPARERWTRPALFIRAT
7299497          YNLRKMQDN--------TFGWAVNPQAVLSSWGEM-MINYEATLGGLRPYMGEVLLIAGS
                  :                :.  :      :        :  .   .

Q57427           NSSYIKIENSEKILEQFPNATAFTINGSGHWVHAEKPDFVIRAIKRFLNKN---------
P75736           NSPYVSEQYRDDLLAQFPQARAHVIAGAGHWVHAEKPDAVLRAIRRYLND---------
Fbh33167F111     NSQFVHPSHHPEIMRLFPRAQMQTVPNAGHWIHADRPQDFIAAIRGFLV---------
3878848          NSGYVPDDHKPDIKCLFPQVQFDAIPDSGHWVHAEKPQLFINSVYKFLKP---------
3876571          GSGFLPAAHKNRVEKMFPMVQFAETAWSNHWIHADDPKFFVDSICEFLEEPDQLGMRAYI
7290805          RSPYMRREQWPQIQKMFPNSEIHWLD-AGHLVHFEKPQEFLTIVSEFLNRTE--------
4049528          KAPFIPDSALPVFKKFFPKYELVSLD-CGHWVHFEKPKEFSESIINFLNN---------
P53219           QSHYVVDEYLPIIGAFFPRFETRDID-AGHWVNAEKPGECAESIVDFVERHED-------
7299497          QSEFVTTTSIAVMQRYFPNTVVQILD-AGHCVYEDQPEQFVELVVEFTQTCLVC------
                 : ::    .   **     ..*  : *     :   :
```

Fig. 5

```
>138325 p99.2 (1) P71702_MYCTU // HYPOTHETICAL 32.1 KD PROTEIN CY21D4.08C
        HYPOTHETICAL PROTEIN
        Length = 298

Score = 173 (66.0 bits), Expect = 1.3e-11, P = 1.3e-11
  Identities = 71/258 (27%), Positives = 115/258 (44%)
Query:    67 PAVVFLHGLFGSKTNFNSIAKILAQQTGRRVLTVDARNHGDSPHSPDMSYEIMSXXXXXX 126
             P V+FLHG  G + N ++   ++       G   L VD  HG S   D +Y
Sbjct:    50 PRVIFLHG--GGQ-NAHTWDTVIVG-LGEPALAVDLPGHGHSAWREDGNYSPQLNSETLA 105

Query:   127 XXXXXXVPCV--VVGHSMGGKTAMLLALQRPELVERLIAVDISPVESTGVSHFATYVAAM 184
                       P   VVG S+GG TA+ LA   P+LV  L+  VD++P  +  +   A  A
Sbjct:   106 PVLRELAPGAEFVVGMSLGGLTAIRLAAMAPDLVGELVLVDVTP---SALQRHAELTAEQ 162

Query:   185 R---AINIAD-ELPRSRARKLADEQLSSVI-QDM-AVRQHLLTNLVEVD-GRFVWRVNLD 237
             R   A+   + E P  +A  + D   +++   +D+ ++R+ +   N    +D G +VWR   D
Sbjct:   163 RGTVALMHGEREFPSFQA--MLDLTIAAAPHRDVKSLRRGVFHNSRRLDNGNWVWRY--D 218

Query:   238 ALTQHLDKILAFPQRQESYLGPTLFLLGGNSQFVHPSHHPEIMRLFPRAQ-MQTVPNAGH 296
             A+     D     ++     P  + GG+S FV    E+ R       + +  V +GH
Sbjct:   219 AIRTFGD-FAGLWDDVDALSAPITLVRGGSSGFVTDQDTAELHRRATHFRGVHIVEKSGH 277

Query:   297 WIHADRPQDFIAAIRGFL 314
             +   +D+P+   I  +RG L
Sbjct:   278 SVQSDQPRALIEIVRGVL 295
```

View Prodom 95 [Boxer ▼] [Showing match ▼] [Go!]

```
>95 p99.2 (304) PIP(9) PRXC(6) LIP(6)  // PROTEIN HYDROLASE TRANSFERASE
    PUTATIVE ESTERASE BIOSYNTHESIS EPOXIDE ACYLTRANSFERASE LIPASE SYNTHASE
    Length = 311

Score = 82 (33.9 bits), Expect = 3.7e-05, Sum P(2) = 3.7e-05
  Identities = 19/61 (31%), Positives = 31/61 (50%)
Query:   259 PTLFLLGGNSQFVHPSHHPEIMR--LFPRAQMQTVPNAGHWIHADRPQD--FIAAIRGFL 314
             PTL + G   Q VP   E+  +    A++ +P AGHW+ ++P++ F I  FL
Sbjct:   225 PTLIIHGEEDQVVPPESSMEKLASTIVSSAELHVIPGAGHWVMMEQPEEMEFNELIMEFL 284

Query:   315 V 315
             +
Sbjct:   285 L 285

Score = 79 (32.9 bits), Expect = 3.7e-05, Sum P(2) = 3.7e-05
  Identities = 36/135 (26%), Positives = 55/135 (40%)
Query:    96 RVLTVDARNHG--DSPH-SPD---MSYEIMSXXXXXXXXXXXXXVPCV-------VVGHSM 142
             RV+  D R +G    D P  SPD    MS  M                +         +VGHSM
Sbjct:    22 RVIAYDMRGYGKSDKPETSPDESSMSEYTMDELADDIAALLDALGIEKAEKKVHLVGHSM 81

Query:   143 GGKTAMLLALQRPELVERLIAVDISPVESTGVSHFATYVAAMRAINIADELPRSRARKLA 202
             GG A+  AL+ PE V+ L +  + +S+  S FA   +M   A+   P
Sbjct:    82 GGAIALQYALRHPERVKSLVLMSAAAMTSS--SDFAM---SMEHRQYAESSPTESVSAAF 136

Query:   203 DEQLSSVIQDMAVRQ 217
             E + +    ++R+
Sbjct:   137 QESMQAETSMQSMRE 151

Score = 44 (20.5 bits), Expect = 0.27, Sum P(2) = 0.24
  Identities = 16/55 (29%), Positives = 25/55 (45%)
Query:   261 LFLLGGNSQFVHPSHHPEIMRLFPRAQMQ-TVPNAGHWIHADRPQDFIAAIRGFL 314
             L ++   G +V   PE M   F     M+  + N+GH   +  + P+ F  +R FL
Sbjct:   256 LHVIPGAGHWVM-MEQPEEME-FNELIMEFLLSNSGHIAFIENPEAFNKILRDFL 308
```

Fig. 6

>39255 p99.2 (2) P76932(1) YFBB(1)   // OF SIMILAR FROM BASES SECTION THE

```
       COMPLETE GENOME PROTEIN MEND-MENB
       Length = 181

Score = 89 (36.4 bits), Expect = 0.034, P = 0.033
 Identities = 25/92 (27%), Positives = 41/92 (44%)

Query:    62 GEAALPAVVFLHGLFGSKTNFNSIAKILAQQTGRRVLTVDARNHGDSPHSPDMSYEIMSX 121
              G+  LP +VFLHG G    +  + A  +     L VD   HG S        ++ ++
Sbjct:    10 GKPGLPWLVFLHGFSGDCHEWQEVGEAFADYSR---LYVDLPGHGGSAAISVDGFDDVTD 66

Query:   122 XXXXXXXXXXXVPCVVVGHSMGGKTAMLLALQ 153
                          +   +VG+S+GG+ AM+ A Q
Sbjct:    67 LLRKTLVSYNILDFWLVGYSLGGRVAMMAACQ 98
```

---

View Prodom 116557 [ Boxer ▼ ] [ Showing match ▼ ] [ Go! ]

>116557 p99.2 (1) O54172_STRCO // HYDROLASE HYDROLASE
Length = 187

```
 Score = 81 (33.6 bits), Expect = 0.33, P = 0.28
 Identities = 30/121 (24%), Positives = 52/121 (42%)

Query:    55 LSYRLLDGEAALPAVVFLHGLFGSKTNFNSIAKILAQQTGRRVLTVDARNHGDSPHSPDM 114
              L    LD  +P ++ +HG    +T F ++   L     G R ++ D R+ G + + P +
Sbjct:    14 LDVGFLDSGDGVP-LLLVHGGESDRTQFATLRAGLG--AGIRAISYDQRDSGITVNPP-V 69

Query:   115 SY--EIMSXXXXXXXXXXXXXXVPCVVVGHSMGGKTAMLLALQRPELVERLIAVDISPVEST 172
              Y   E+++                ++G S GG  A   A + PE V  L+ + V  +P +
Sbjct:    70 PYTPEVLADDLVDLLDALGLARAHLLGTSFGGAVAQHAARRHPERVASLVLVATTPSYAM 129

Query:   173 G 173
              G
Sbjct:   130 G 130
```

---

View Prodom 119335 [ Boxer ▼ ] [ Showing match ▼ ] [ Go! ]

>119335 p99.2 (1) O86608_STRCO // 3-OXOADIPATE ENOL-LACTONE
HYDROLASE/4-CARBOXYMUCONOLACTONE DECARBOXYLASE HYDROLASE
Length = 185

```
 Score = 74 (31.1 bits), Expect = 2.1, P = 0.87
 Identities = 37/142 (26%), Positives = 52/142 (36%)

Query:    55 LSYRLLDGEAALPAVVFLHGLFGSKTNFNSIAKILAQQTGRRVLTVDARNHGDSPHSPDM 114
              L YR  DG     P ++  L   +          LAQQ   RV  D    HG +P    P
Sbjct:     9 LQYRF-DGPEEAPVLILGPSLGTTWHMWDRQVPELAQQW--RVFRFDLPGHGGAPAHAG 65

Query:   115 SYEIMSXXXXXXXXXXXXXXVPCVVVGHSMGGKTAMLLALQRPELVERLIAVDISPVESTGV 174
              S  ++                 G + GG  +  LAL+  PE  + L   +  SP     T
Sbjct:    66 SVAELTTRLLATLDGLGVQRFGYAGCAFGGAVGIELALRHPERLASLALIAASPRFGTA- 124

Query:   175 SHFATYVAAMRAINIADELPRS 196
                F      +R N D + RS
Sbjct:   125 DEFRQRGVIVRT-NGLDPIARS 145
```

Fig. 6
continued

33167, A NOVEL HUMAN HYDROLASE AND USES THEREFOR

RELATED APPLICATIONS

This application claims priority to U.S. Provisional Patent Application No. 60/193,954 filed on Mar. 31, 2000, incorporated herein in its entirety by reference.

BACKGROUND OF THE INVENTION

The hydrolysis of chemical bonds within molecules is of critical importance in most metabolic (e.g., catabolic and anabolic) pathways in cells. A large family of enzymes which catalyze the cleavage of a bond with the addition of water, termed hydrolases, has been identified. Members of the hydrolase family are found in nearly all organisms, from microbes to plants to humans. Different classes of hydrolases are specific for an array of biological and chemical substrates. Members of the hydrolase family of enzymes include enzymes that hydrolyze ester bonds (e.g., phosphatases, sulfatases, exonucleases, and endonucleases), glycosidases, enzymes that act on ether bonds, peptidases (e.g., exopeptidases and endopeptidases), as well as enzymes that hydrolyze carbon-nitrogen bonds, acid anhydrides, carbon-carbon bonds, halide bonds, phosphorous-nitrogen bonds, sulfur-nitrogen bonds, carbon-phosphorous bonds, and sulfur-sulfur bonds (E. C. Webb ed., *Enzyme Nomenclature*, pp. 306–450, ©1992 Academic Press, Inc. San Diego, Calif.).

Hydrolases vary widely in primary sequence, substrate specificity, and physical properties. However, despite the lack of sequence homology, hydrolase family members display structural similarities, e.g., conservation of a catalytic site framework. For example, the alpha/beta hydrolase fold is a structural motif that is common to a variety of hydrolytic enzymes including, lipases, e.g., fungal, bacterial and pancreatic lipase, acetylcholinesterases, serine carboxypeptidases, haloalkane dehalogenases, dienelactone hydrolases, $A_2$ bromoperoxidases, and thioesterases (Schrag, J. et al. (1997) *Meth. Enzymol.* 284:85–107). Enzymes possessing the alpha/beta hydrolase fold have diverged from a common ancestor so as to preserve the arrangement of the catalytic residues (Ollis, D. et al. (1992) *Protein Eng.* 5:197–211). In particular, one conserved feature of the alpha/beta hydrolase fold is a nucleophile-histidine-acid catalytic triad. The identities of the triad residues in alpha/beta hydrolase fold enzymes are quite variable in that serine, aspartate, and cysteine have all been identified as catalytic nucleophiles (Schrag, J. et al. supra).

Hydrolases play important roles in the synthesis and breakdown of nearly all major metabolic intermediates, including polypeptides, nucleic acids, and lipids. As such, their activity contributes to the ability of the cell to grow and differentiate, to proliferate, to adhere and move, and to interact and communicate with other cells. Hydrolases also are important in the conversion of pro-proteins and pro-hormones to their active forms, the inactivation of peptides, the biotransformation of compounds (e.g., a toxin or carcinogen), antigen presentation, and the regulation of synaptic transmission.

SUMMARY OF THE INVENTION

The present invention is based, at least in part, on the discovery of novel members of the family of hydrolase molecules, referred to herein as "hydrolase-1" or "HYDL-1" nucleic acid and protein molecules. The HYDL-1 nucleic acid and protein molecules of the present invention are useful as modulating agents in regulating a variety of cellular processes, e.g., cellular proliferation, growth, differentiation, or migration. Accordingly, in one aspect, this invention provides isolated nucleic acid molecules encoding HYDL-1 proteins or biologically active portions thereof, as well as nucleic acid fragments suitable as primers or hybridization probes for the detection of HYDL-1-encoding nucleic acids.

In one embodiment, an HYDL-1 nucleic acid molecule of the invention is at least 50%, 55%, 60%, 65%, 70%, 74%, 75%, 80%, 85%, 89%, 90%, 95%, 96%, 97%, 98%, 99% or more identical to the nucleotide sequence (e.g., to the entire length of the nucleotide sequence) shown in SEQ ID NO:1 or 3.

In a preferred embodiment, the isolated nucleic acid molecule includes the nucleotide sequence shown in SEQ ID NO:1 or 3, or a complement thereof. In another embodiment, the nucleic acid molecule includes SEQ ID NO:3 and nucleotides 1–46 of SEQ ID NO:1. In yet a further embodiment, the nucleic acid molecule includes SEQ ID NO:3 and nucleotides 995–1332 of SEQ ID NO:1. In another preferred embodiment, the nucleic acid molecule consists of the nucleotide sequence shown in SEQ ID NO: 1 or 3.

In another embodiment, an HYDL-1 nucleic acid molecule includes a nucleotide sequence encoding a protein having an amino acid sequence sufficiently identical to the amino acid sequence of SEQ ID NO:2. In a preferred embodiment, an HYDL-1 nucleic acid molecule includes a nucleotide sequence encoding a protein having an amino acid sequence at least 50%, 55%, 60%, 65%, 70%, 74%, 75%, 80%, 85%, 89%, 90%, 95%, 96%, 97%, 98%, 99% or more identical to the entire length of the amino acid sequence of SEQ ID NO:2.

In another preferred embodiment, an isolated nucleic acid molecule encodes the amino acid sequence of human HYDL- 1. In yet another preferred embodiment, the nucleic acid molecule includes a nucleotide sequence encoding a protein having the amino acid sequence of SEQ ID NO:2. In yet another preferred embodiment, the nucleic acid molecule is at least 50, 100, 150, 200, 250, 300, 350, 400, 450, 500, 550, 600, 650, 653, 700, 750, 800, 850, 900, 950, 1000, 1100, 1200, 1300 or more nucleotides in length. In a further preferred embodiment, the nucleic acid molecule is at least 50, 100, 150, 200, 250, 300, 350, 400, 450, 500, 550, 600, 650, 653, 700, 750, 800, 850, 900, 950, 1000, 1100, 1200, 1300 or more nucleotides in length and encodes a protein having an HYDL-1 activity (as described herein).

Another embodiment of the invention features nucleic acid molecules, preferably HYDL-1 nucleic acid molecules, which specifically detect HYDL-1 nucleic acid molecules relative to nucleic acid molecules encoding non-HYDL-1 proteins. For example, in one embodiment, such a nucleic acid molecule is at least 20, 30, 40, 50, 100, 150, 200, 250, 300, 350, 400, 450, 500, 550, 600, 650, 653, 700, 750, 800, 850, 900, 950, 1000, 1100, 1200, 1300 or more nucleotides in length and hybridizes under stringent conditions to a nucleic acid molecule comprising the nucleotide sequence shown in SEQ ID NO:1 or 3.

In preferred embodiments, the nucleic acid molecules are at least 15 nucleotides (e.g., 15 contiguous nucleotides) in length and hybridize under stringent conditions to the nucleotide molecules set forth in SEQ ID NO:1 or 3 or a complement thereof. In certain embodiments, the nucleic acid molecules are at least 15 nucleotides in length and hybridize under stringent conditions to nucleotides 1–23 and 1002–1332 of SEQ ID NO:1. In another embodiment, the nucleic acid molecules comprise nucleotides 1–23 and 1002–1332 of SEQ ID NO:1. In yet another embodiment, the nucleic acid molecules consist of nucleotides 1–23 and 1002–1332 of SEQ ID NO:1.

In other preferred embodiments, the nucleic acid molecule encodes a naturally occurring allelic variant of a polypeptide comprising the amino acid sequence of SEQ ID NO:2., wherein the nucleic acid molecule hybridizes to a nucleic acid molecule comprising SEQ ID NO:1 or 3 under stringent conditions.

Another embodiment of the invention provides an isolated nucleic acid molecule which is antisense to a HYDL-1 nucleic acid molecule, e.g., the coding strand of an HYDL-1 nucleic acid molecule.

Another aspect of the invention provides a vector comprising an HYDL-1 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an HYDL-1 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant HYDL-1 proteins and polypeptides. In one embodiment, an isolated HYDL-1 protein includes at least one or more of the following domains: an alpha/beta hydrolase fold, a transmembrane domain, or a signal peptide. In a preferred embodiment, an isolated HYDL-1 protein includes at least one alpha/beta hydrolase fold.

In a preferred embodiment, an HYDL-1 protein includes at least one or more of the following domains: an alpha/beta hydrolase fold, a transmembrane domain, or a signal peptide, and has an amino acid sequence at least about 50%, 55%, 60%, 65%, 67%, 68%, 70%, 72%, 75%, 80%, 85%, 87%, 90%, 95%, 96%, 97%, 98%, 99% or more identical to the amino acid sequence of SEQ ID NO:2. In another preferred embodiment, an HYDL-1 protein includes at least one or more of the following domains: an alpha/beta hydrolase fold, a transmembrane domain, or a signal peptide, and has an HYDL-1 activity (as described herein).

In yet another preferred embodiment, an HYDL-1 protein includes at least one or more of the following domains: an alpha/beta hydrolase fold, a transmembrane domain, or a signal peptide, and is encoded by a nucleic acid molecule having a nucleotide sequence which hybridizes under stringent hybridization conditions to a nucleic acid molecule comprising the nucleotide sequence of SEQ ID NO:1 or 3.

In another embodiment, the invention features fragments of the protein having the amino acid sequence of SEQ ID NO:2, wherein the fragment comprises at least 15 amino acids (e.g., contiguous amino acids) of the amino acid sequence of SEQ ID NO:2. In another embodiment, an HYDL-1 protein has the amino acid sequence of SEQ ID NO:2.

In another embodiment, the invention features an HYDL-1 protein which is encoded by a nucleic acid molecule consisting of a nucleotide sequence at least about 50%, 55%, 60%, 65%, 70%, 72%, 75%, 80%, 85%, 87%, 90%, 95%, 96%, 97%, 98%, 99% or more identical to a nucleotide sequence of SEQ ID NO:1 or 3, or a complement thereof.

This invention further features an HYDL-1 protein which is encoded by a nucleic acid molecule consisting of a nucleotide sequence which hybridizes under stringent hybridization conditions to a nucleic acid molecule comprising the nucleotide sequence of SEQ ID NO:1 or 3, or a complement thereof.

The proteins of the present invention or portions thereof, e.g., biologically active portions thereof, can be operatively linked to a non-HYDL-1 polypeptide (e.g., heterologous amino acid sequences) to form fusion proteins. The invention further features antibodies, such as monoclonal or polyclonal antibodies, that specifically bind proteins of the invention, preferably HYDL-1 proteins. In addition, the HYDL-1 proteins or biologically active portions thereof can be incorporated into pharmaceutical compositions, which optionally include pharmaceutically acceptable carriers.

In another aspect, the present invention provides a method for detecting the presence of an HYDL-1 nucleic acid molecule, protein, or polypeptide in a biological sample by contacting the biological sample with an agent capable of detecting an HYDL-1 nucleic acid molecule, protein, or polypeptide such that the presence of an HYDL-1 nucleic acid molecule, protein or polypeptide is detected in the biological sample.

In another aspect, the present invention provides a method for detecting the presence of HYDL-1 activity in a biological sample by contacting the biological sample with an agent capable of detecting an indicator of HYDL-1 activity such that the presence of HYDL-1 activity is detected in the biological sample.

In another aspect, the invention provides a method for modulating HYDL-1 activity comprising contacting a cell capable of expressing HYDL-1 with an agent that modulates HYDL-1 activity such that HYDL-1 activity in the cell is modulated. In one embodiment, the agent inhibits HYDL-1 activity. In another embodiment, the agent stimulates HYDL-1 activity. In one embodiment, the agent is an antibody that specifically binds to an HYDL-1 protein. In another embodiment, the agent modulates expression of HYDL-1 by modulating transcription of an HYDL-1 gene or translation of an HYDL-1 mRNA. In yet another embodiment, the agent is a nucleic acid molecule having a nucleotide sequence that is antisense to the coding strand of an HYDL-1 mRNA or a HYDL-1 gene.

In one embodiment, the methods of the present invention are used to treat a subject having a disorder characterized by aberrant or unwanted HYDL-1 protein or nucleic acid expression or activity by administering an agent which is an HYDL-1 modulator to the subject. In one embodiment, the HYDL-1 modulator is an HYDL-1 protein. In another embodiment the HYDL-1 modulator is an HYDL-1 nucleic acid molecule. In yet another embodiment, the HYDL-1 modulator is a peptide, peptidomimetic, or other small molecule. In a preferred embodiment, the disorder characterized by aberrant or unwanted HYDL-1 protein or nucleic acid expression is a hydrolase-associated disorder, e.g., a central nervous system (CNS) disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. In another preferred embodiment, the disorder characterized by aberrant or unwanted HYDL-1 protein or nucleic acid expression is a cancer, e.g., lung cancer.

The present invention also provides diagnostic assays for identifying the presence or absence of a genetic alteration characterized by at least one of (i) aberrant modification or mutation of a gene encoding an HYDL-1 protein; (ii) mis-regulation of the gene; and (iii) aberrant post-translational modification of an HYDL-1 protein, wherein a wild-type form of the gene encodes a protein with an HYDL-1 activity.

In another aspect the invention provides methods for identifying a compound that binds to or modulates the activity of an HYDL-1 protein, by providing an indicator composition comprising an HYDL-1 protein having HYDL-1 activity, contacting the indicator composition with a test compound, and determining the effect of the test compound on HYDL-1 activity in the indicator composition to identify a compound that modulates the activity of a HYDL-1 protein.

Accordingly, the present invention provides methods and compositions for the diagnosis and treatment of cellular proliferative disorders, including but not limited to cancer, e.g., lung, colon and breast cancer.

Other features and advantages of the invention will be apparent from the following detailed description and claims.

BRIEF DESCRIPTION OF THE DRAWINGS

FIG. 1 depicts the cDNA sequence and predicted amino acid sequence of human HYDL-1 (clone Fbh33167F11). The nucleotide sequence corresponds to nucleic acids 1 to 1332 of SEQ ID NO:1. The amino acid sequence corresponds to amino acids 1 to 315 of SEQ ID NO:2. The coding region without the 3' untranslated region of the human HYDL-1 gene is shown in SEQ ID NO:3.

FIG. 3 depicts the results of a search which was performed against the MEMSAT database and which resulted in the identification of two "transmembrane domains" in the human HYDL-1 protein (SEQ ID NO:2).

FIG. 4 depicts the results of a search which was performed against the HMM database and which resulted in the identification of an "alpha/beta hydrolase fold" in the human HYDL-1 protein.

FIG. 5 depicts the alignment of human HYDL-1 with the Y193_HAEIN putative esterase/lipase H10193 (Accession No. Q57427, SEQ ID NO:4), the YBFF_ECOLI putative esterase/lipase YBFF (Accession No. P75736, SEQ ID NO:5), *C. elegans* (Z81105) similar to alpha/beta hydrolase fold (Accession No. CAB03219, SEQ ID NO:6), the *C. elegans* (Z81522) predicted similar to alpha/beta hydrolase fold (Accession No. CAB04232, SEQ ID NO:7), the *Drosophila melanogaster* CG2059 gene product (Accession No. AAF46249, SEQ ID NO:8), *Schizosaccharomyces pombe* hypothetical alpha/beta hydrolase fold domain protein (Accession No. CAA22555, SEQ ID NO:9), the YGIL_YEASR hypothethical 38.5 KDa protein in ERV1-GLS2 intergenic region (Accession No. P53219, SEQ ID NO:10), and the *Drosophila melanogaster* CG14717 gene product (Accession No. AAF54685, SEQ ID NO:11). These alignments were generated using the Clustal W (1.74) multiple sequence alignment.

FIG. 6 depicts the results of a search which was performed against the ProDom database and which resulted in the local alignment of the human HYDL-1 protein with p99.2 (1) P71702_MYCTU; p99.2 (304) PIP (9) PRXC (6) LIP (6); p99.2 (2) P76932(1) YFBB (1); p99.2 (1) O54172_STRCO; and p99.2 (1) O86608_STRCO.

DETAILED DESVRIPTION OF THE INVENTION

Figure 2:
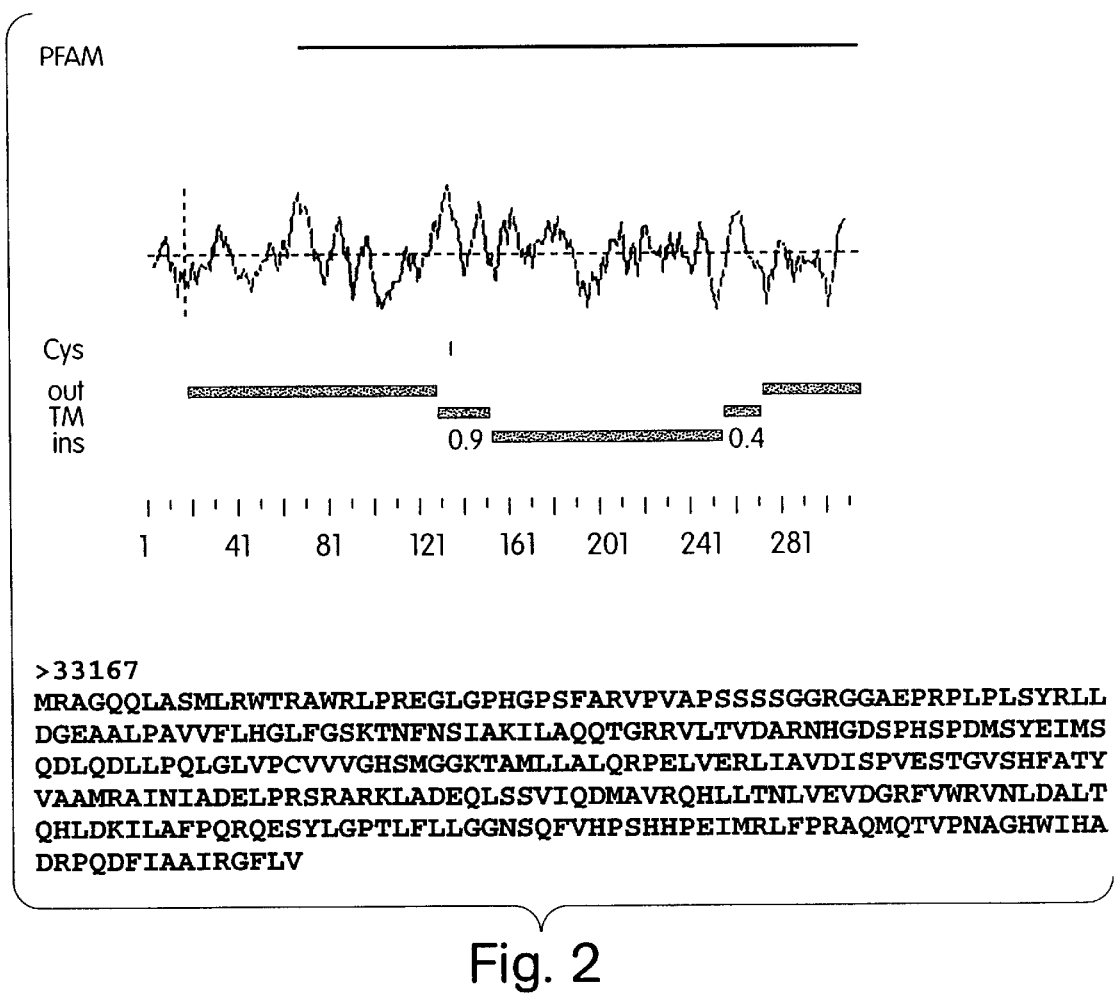
FIG. 2 depicts a structural, hydrophobicity, and antigenicity analysis of the human HYDL-1 protein.

The present invention is based, at least in part, on the discovery of novel molecules, referred to herein as "hydrolase-1" or "HYDL-1" nucleic acid and protein molecules, which are novel members of a family of enzymes which are capable of catalyzing the hydrolytic cleavage of a chemical bond (e.g., a chemical bond within a biological molecule). Thus, these novel HYDL-1 molecules may play a role in or function in a variety of metabolic and cellular processes, e.g., proliferation, growth, differentiation, migration, biotransformation, immune responses, hormonal responses, and inter- or intra-cellular communication.

As used herein, the term "hydrolase" includes a molecule which is involved in the hydrolytic cleavage of a bond within a biological molecule (e.g., a peptide, a lipid, or a nucleic acid). Hydrolase molecules are involved in the anabolism and catabolism of metabolically important biomolecules, including the metabolism of biochemical molecules necessary for energy production or storage, and for intra- or inter-cellular signaling, as well as the detoxification of potentially harmful compounds (e.g., toxins, carcinogens). Examples of hydrolases include fungal, bacterial and pancreatic lipases, acetylcholinesterases, serine carboxypeptidases, haloalkane dehalogenases, dienelactone hydrolases, $A_2$bromoperoxidases, and thioesterases. As hydrolases, the HYDL-1 molecules of the present invention provide novel diagnostic targets and therapeutic agents to control hydrolase-associated disorders.

As used herein, a "hydrolase-associated disorder" or an "HYDL-1 associated disorder" includes a disorder, disease or condition which is caused or characterized by a misregulation (e.g., downregulation or upregulation) of an HYDL-1-mediated activity. Hydrolase-associated disorders can detrimentally affect cellular functions such as cellular proliferation, growth, differentiation, or migration, inter- or intra-cellular communication; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, or mutagens). Examples of hydrolase-associated disorders include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The HYDL-1 molecules of the present invention are involved in metabolic mechanisms which are known to be involved in cellular growth, differentiation, and migration processes. Thus, the HYDL-1 molecules may modulate cellular growth, differentiation, or migration, and may play a role in disorders characterized by aberrantly regulated growth, differentiation, or migration. Such disorders include cancer (e.g., carcinoma, sarcoma, or leukemia), examples of which include, but are not limited to, lung, breast, endometrial, ovarian, uterine, hepatic, gastrointestinal, prostate, and colorectal cancer, melanoma, neurofibromatosis, adenomatous polyposis of the colon, Wilms' tumor, nephroblastoma, teratoma, rhabdomyosarcoma;. tumor invasion, angiogenesis and metastasis; skeletal dysplasia; hematopoietic and/or myeloproliferative disorders.

HYDL-1 disorders also include central nervous system (CNS) disorders such as cognitive and neurodegenerative disorders, examples of which include, but are not limited to, Alzheimer's disease, dementias related to Alzheimer's disease (such as Pick's disease), PARKINSON's and other Lewy diffuse body diseases, senile dementia, myasthenia gravis, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of hydrolase-associated disorders include cardiac-related disorders. Cardiovascular system disorders in which the HYDL-1 molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. HYDL-1 mediated or related disorders also include disorders of the musculoskeletal system such as paralysis and muscle weakness, e.g., ataxia, myotonia, and myokymia.

HYDL-1 associated or related disorders also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

HYDL-1-associated or related disorders also include inflammatory or immune system disorders, examples of which include, but are not limited to viral infection, inflammatory bowel disease, ulcerative colitis, Crohn's disease, leukocyte adhesion deficiency II syndrome, peritonitis, chronic obstructive pulmonary disease, lung inflammation, asthma, acute appendicitis, septic shock, nephritis, amyloidosis, rheumatoid arthritis, chronic bronchitis, sarcoidosis, scleroderma, lupus, polymyositis, Reiter's syndrome, psoriasis, pelvic inflammatory disease, inflammatory breast disease, orbital inflammatory disease, immune deficiency disorders (e.g., HIV, common variable immunodeficiency, congenital X-linked infantile hypogammaglobulinemia, transient hypogammaglobulinemia, selective IgA deficiency, chronic mucocutaneous candidiasis, severe combined immunodeficiency), autoimmune disorders.

An HYDL-1 associated disorder also includes a hematopoietic or thrombotic disorder, for example, disseminated intravascular coagulation, thromboembolic vascular disease, anemia, lymphoma, leukemia, neutrophilia, neutropenia, myeloproliferative disorders, thrombocytosis, thrombocytopenia, vonWillebrand disease, and hemophilia.

In addition, HYDL-1 associated disorders include gastrointestinal and digestive disorders including, but not limited to, esophageal disorders such as atresia and fistulas, stenosis, achalasia, esophageal rings and webs, hiatal hernia, lacerations, esophagitis, diverticula, systemic sclerosis (scleroderma), varices, esophageal tumors such as squamous cell carcinomas and adenocarcinomas, stomach disorders such as diaphragmatic hernias, pyloric stenosis, dyspepsia, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas; as well as metabolic disorders (e.g., lysosomal storage disease, type II glycogenolysis, Fabry's disease, enzyme deficiencies, and inborn errors of metabolism); hepatic disorders and renal disorders (e.g., renal failure and glomerulonephritis).

HYDL-1-associated or related disorders also include disorders affecting tissues in which HYDL-1 protein is expressed.

As used herein, a "hydrolase-mediated activity" or an "HYDL-1-mediated activity" includes an activity which involves the cleavage, e.g., hydrolytic cleavage, of a chemical bond within a biochemical molecule, e.g., a biochemical molecule that is associated with the regulation of one or more cellular processes, such as a peptide, a nucleic acid, a lipid or a vitamin. Hydrolase-mediated activities include the anabolism and catabolism of metabolically important biomolecules, including the metabolism of biochemical molecules necessary for energy production or storage, and for intra- or inter-cellular signaling, as well as the detoxification of potentially harmful compounds.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or nonnaturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, the family of HYDL-1 proteins comprises at least one "alpha/beta hydrolase fold" in the protein or corresponding nucleic acid molecule. As used herein, the term "alpha/beta hydrolase fold" includes a protein tertiary (i.e., three dimensional) structure that preferably has an $\alpha/\beta$ sheet of $\beta$-strands (e.g., eight $\beta$ strands) connected by $\alpha$-helices. In one embodiment, an alpha/beta hydrolase fold comprises a catalytic triad. In a further embodiment, an alpha/beta hydrolase fold comprises a nucleophile-histidine-acid catalytic triad. In one embodiment, the acid in the catalytic triad can be either glutamate or aspartate. In another embodiment, the nucleophile in the catalytic triad can be either serine, cysteine or aspartate. The catalytic triad of the HYDL-1 molecules of the present invention (SEQ ID NO:2) comprises $Ser^{141}$ and $His^{296}$. Alpha/beta hydrolase fold structures are described in, for example, in Ollis, D. et al. (1992) *Protein Eng.* 5:197–211, the contents of which are incorporated herein by reference. The term alpha/beta hydrolase fold includes a protein domain having an amino acid sequence of about 100–500 amino acid residues, preferably about 150–350 amino acid residues, and more preferably about 200–250 amino acid residues, and having a bit score for the alignment of the sequence to the alpha/beta hydrolase fold (HMM) of at least about 40, more preferably 50, 60, 70, 80, 83 or greater. To identify the presence of an alpha/beta hydrolase fold in an HYDL-1 protein, and to make the determination that a protein of interest has a particular profile, the amino acid sequence of the protein is searched against a database of known protein domains (e.g., the HMM database). The alpha/beta hydrolase fold (HMM) has been assigned the PFAM Accession PF00561 (http://genome.wustl.edu/Pfam/html). A search was performed against the HMM database resulting in the identification of an alpha/beta hydrolase fold in the amino acid sequence of human HYDL-1 (SEQ ID NO:2) at about residues 95–314 of SEQ ID NO:2. The results of the search are set forth in FIG. 4.

In one embodiment, an alpha/beta hydrolase fold includes at least about 150–300 amino acid residues and has at least about 50–60% homology with an alpha/beta hydrolase fold of human HYDL-1 (e.g., residues 95–314 of SEQ ID NO:2). Preferably, an alpha/beta hydrolase fold includes at least about 175–275 amino acid residues, or about 200–250 amino acid residues, and has at least 60–70% homology, preferably about 70–80%, or about 80–90% homology with an alpha/beta hydrolase fold of human HYDL-1 (e.g., residues 95–314 of SEQ ID NO:2).

Accordingly, HYDL-1 proteins having at least 50–60% homology, preferably about 60–70%, more preferably about 70–80%, or about 80–90% homology with an alpha/beta hydrolase fold of human HYDL-1 are within the scope of the invention.

In another embodiment, an HYDL-1 protein of the present invention is identified based on the presence of a at least one "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neurosci.* 19: 235–263, the contents of which are incorporated herein by reference. Amino acid residues 130–152 and 255–271 of the native HYDL-1 protein are predicted to comprise a transmembrane domain (see FIG. 3). Accordingly, HYDL-1 proteins having at least 50–60% homology, preferably about 60–70%, more preferably about 70–80%, or about 80–90% homology with a transmembrane domain of human HYDL-1 are within the scope of the invention.

In another embodiment of the invention, an HYDL-1 protein of the present invention is identified based on the presence of a signal peptide. The prediction of such a signal peptide can be made, for example, utilizing the computer algorithm SignalP (Henrik, et al. (1997) *Protein Engineering* 10:1–6). As used herein, a "signal sequence" or "signal peptide" includes a peptide containing about 15 or more amino acids which occurs at the N-terminus of secretory and membrane bound proteins and which contains a large number of hydrophobic amino acid residues. For example, a signal sequence contains at least about 10–30 amino acid residues, preferably about 15–25 amino acid residues, more preferably about 18–20 amino acid residues, and more preferably about 19 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer, and is cleaved in secreted and membrane bound proteins. A putative signal sequence was identified in the amino acid sequence of human HYDL-1 at about amino acids 1–16 of SEQ ID NO:2.

In a preferred embodiment, the HYDL-1 molecules of the invention include at least one or more of the following domains: an alpha/beta hydrolase fold, a transmembrane domain, or a signal peptide. In a further preferred embodiment, the HYDL-1 molecules of the invention include at least one alpha/beta hydrolase fold.

Isolated proteins of the present invention, preferably HYDL-1 proteins, have an amino acid sequence sufficiently identical to the amino acid sequence of SEQ ID NO:2, or are encoded by a nucleotide sequence sufficiently identical to SEQ ID NO:1 or 3. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, an "HYDL-1 activity", "biological activity of HYDL-1" or "HYDL-1-mediated activity", includes an activity exerted by an HYDL-1 protein, polypeptide or nucleic acid molecule on an HYDL-1 responsive cell or tissue, or on an HYDL-1 protein substrate, as determined in vivo, or in vitro, according to standard techniques. In one embodiment, an HYDL-1 activity is a direct activity, such as an association with an HYDL-1 target molecule. As used herein, a "target molecule" or "binding partner" is a molecule with which an HYDL-1 protein binds or interacts in nature, such that HYDL-1 mediated function is achieved. An HYDL-1 target molecule can be a non-HYDL-1 molecule or an HYDL-1 protein or polypeptide of the present invention. In an exemplary embodiment, an HYDL-1 target molecule is an HYDL-1 substrate (e.g., a peptide, a lipid, a nucleic acid, or a vitamin). Alternatively, an HYDL-1 activity is an indirect activity, such as a cellular signaling activity mediated by interaction of the HYDL-1 protein with an HYDL-1 ligand or substrate. The biological activities of HYDL-1 are described herein. For example, the HYDL-1 proteins of the present invention can have one or more of the following activities: 1) modulation of the metabolism of biochemical molecules necessary for energy production or storage, 2) modulation of the conversion of pro-proteins and/or pro-hormones to their active forms; 3) modulation of the inactivation of peptides; 4) modulation of intra- or inter-cellular signaling; 5) modulation of the biotransformation and detoxification of potentially harmful compounds; and 6) modulation of the anabolism and/or catabolism of metabolically important biomolecules.

In one embodiment, an HYDL-1 activity is a thioesterase activity. In another embodiment, an HYDL-1 activity is a lipase activity.

Accordingly, another embodiment of the invention features isolated HYDL-1 proteins and polypeptides having an HYDL-1 activity. Other preferred proteins are HYDL-1 proteins having one or more of the following domains: alpha/beta hydrolase fold, a transmembrane domain, or a signal peptide and, preferably, an HYDL-1 activity.

Additional preferred proteins have at least one alpha/beta hydrolase fold, and one or more of a transmembrane domain, or a signal peptide, and are, preferably, encoded by a nucleic acid molecule having a nucleotide sequence which hybridizes under stringent hybridization conditions to a nucleic acid molecule comprising the nucleotide sequence of SEQ ID NO:1 or 3.

The nucleotide sequence of the isolated human HYDL-1 cDNA and the predicted amino acid sequence of the human HYDL-1 polypeptide are shown in FIG. 1 and in SEQ ID NOs:1 and 2, respectively.

The human HYDL-1 gene, which is approximately 1332 nucleotides in length, encodes a protein having a molecular weight of approximately 35 kD and which is approximately 315 amino acid residues in length.

Various aspects of the invention are described in further detail in the following subsections:

I. Isolated Nucleic Acid Molecules

One aspect of the invention pertains to isolated nucleic acid molecules that encode HYDL-1 proteins or biologically active portions thereof, as well as nucleic acid fragments sufficient for use as hybridization probes to identify HYDL-1-encoding nucleic acid molecules (e.g., HYDL-1 mRNA) and fragments for use as PCR primers for the amplification or mutation of HYDL-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated HYDL-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or a portion thereof, can be isolated using standard molecular biology techniques and the sequence information provided herein. Using all or portion of the nucleic acid sequence of SEQ ID NO:1 or 3, HYDL-1 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to HYDL-1 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1 or 3. This cDNA may comprise sequences encoding the human HYDL-1 protein (i.e., "the coding region", from nucleotides 47–994), as well as 5' untranslated sequences (nucleotides 1–46) and 3' untranslated sequences (nucleotides 995–1332) of SEQ ID NO:1. Alternatively, the nucleic acid molecule can comprise only the coding region of SEQ ID NO:1 (e.g., nucleotides 47–994, corresponding to SEQ ID NO:3).

In another preferred embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3 is one which is sufficiently complementary to the nucleotide sequence shown in SEQ ID NO:1 or 3 such that it can hybridize to the nucleotide sequence shown in SEQ ID NO:1 or 3 respectively, thereby forming a stable duplex.

In still another preferred embodiment, an isolated nucleic acid molecule of the present invention comprises a nucleotide sequence which is at least about 50%, 55%, 60%, 65%, 70%, 74%, 75%, 80%, 85%, 89%, 90%, 95%, 96%, 97%, 98%, 99% or more identical to the entire length of the nucleotide sequence shown in SEQ ID NO:1 or 3, or a portion of any of these nucleotide sequences.

Moreover, the nucleic acid molecule of the invention can comprise only a portion of the nucleic acid sequence of SEQ ID NO:1 or 3, for example, a fragment which can be used as a probe or primer or a fragment encoding a portion of an HYDL-1 protein, e.g., a biologically active portion of an HYDL-1 protein. The nucleotide sequences determined from the cloning of the HYDL-1 gene allows for the generation of probes and primers designed for use in identifying and/or cloning other HYDL-1 family members, as well as HYDL-1 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3 of an anti-sense sequence of SEQ ID NO:1 or 3 or of a naturally occurring allelic variant or mutant of SEQ ID NO:1 or 3. In one embodiment, a nucleic acid molecule of the present invention comprises a nucleotide sequence which is greater than 50–100, 100–150, 150–200, 200–250, 250–300, 300–350, 350–400, 400–450, 450–500, 500–550, 550–600, 600–650, 653, 653–700, 700–750, 750–800, 800–850, 850–900, 900–950, 950–1000, 1000–1100, 1100–1200, 1200–1300 or more nucleotides in length and hybridizes under stringent hybridization conditions to a nucleic acid molecule of SEQ ID NO:1 or 3.

Probes based on the HYDL-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an HYDL-1 protein, such as by measuring a level of an HYDL-1-encoding nucleic acid in a sample of cells from a subject e.g., detecting HYDL-1 MRNA levels or determining whether a genomic HYDL-1 gene has been mutated or deleted.

A nucleic acid fragment encoding a "biologically active portion of an HYDL-1 protein" can be prepared by isolating a portion of the nucleotide sequence of SEQ ID NO:1 or 3, which encodes a polypeptide having an HYDL-1 biological activity (the biological activities of the HYDL-1 proteins are described herein), expressing the encoded portion of the HYDL-1 protein (e.g., by recombinant expression in vitro) and assessing the activity of the encoded portion of the HYDL-1 protein.

The invention further encompasses nucleic acid molecules that differ from the nucleotide sequence shown in SEQ ID NO:1 or 3 due to degeneracy of the genetic code and thus encode the same HYDL-1 proteins as those encoded by the nucleotide sequence shown in SEQ ID NO:1 or 3. In another embodiment, an isolated nucleic acid molecule of the invention has a nucleotide sequence encoding a protein having an amino acid sequence shown in SEQ ID NO:2.

In addition to the HYDL-1 nucleotide sequences shown in SEQ ID NO:1 or 3, it will be appreciated by those skilled in the art that DNA sequence polymorphisms that lead to changes in the amino acid sequences of the HYDL-1 proteins may exist within a population (e.g., the human population). Such genetic polymorphism in the HYDL-1 genes may exist among individuals within a population due to natural allelic variation. As used herein, the terms "gene" and "recombinant gene" refer to nucleic acid molecules which include an open reading frame encoding an HYDL-1 protein, preferably a mammalian HYDL-1 protein, and can further include non-coding regulatory sequences, and introns.

Allelic variants of human HYDL-1 include both functional and non-functional HYDL-1 proteins. Functional allelic variants are naturally occurring amino acid sequence variants of the human HYDL-1 protein that maintain the ability to bind an HYDL-1 ligand or substrate and/or modulate cell proliferation and/or migration mechanisms, or metabolism of biochemical molecules (e.g., a peptide, lipid or nucleic acid). Functional allelic variants will typically contain only conservative substitution of one or more amino acids of SEQ ID NO:2, or substitution, deletion or insertion of non-critical residues in non-critical regions of the protein.

Non-functional allelic variants are naturally occurring amino acid sequence variants of the human HYDL-1 protein that do not have the ability to either bind an HYDL-1 ligand or substrate and/or modulate any of the HYDL-1 activities described herein. Non-functional allelic variants will typically contain a non-conservative substitution, a deletion, or insertion or premature truncation of the amino acid sequence of SEQ ID NO:2, or a substitution, insertion or deletion in critical residues or critical regions of the protein.

The present invention further provides non-human orthologues of the human HYDL-1 protein. Orthologues of the human HYDL-1 protein are proteins that are isolated from non-human organisms and possess the same HYDL-1 ligand or substrate binding and/or modulation of cell proliferation and/or migration mechanisms, or metabolism of biochemical molecules of the human HYDL-1 protein. Orthologues of the human HYDL-1 protein can readily be identified as comprising an amino acid sequence that is substantially identical to SEQ ID NO:2.

Moreover, nucleic acid molecules encoding other HYDL-1 family members and, thus, which have a nucleotide sequence which differs from the HYDL-1 sequence of SEQ ID NO:1 or 3 are intended to be within the scope of the invention. For example, another HYDL-1 cDNA can be identified based on the nucleotide sequence of human HYDL. Moreover, nucleic acid molecules encoding HYDL-1 proteins from different species, and which, thus, have a nucleotide sequence which differs from the HYDL-1 sequence of SEQ ID NO:1 or 3 are intended to be within the scope of the invention. For example, a mouse HYDL-1 cDNA can be identified based on the nucleotide sequence of a human HYDL-1.

Nucleic acid molecules corresponding to natural allelic variants and homologues of the HYDL-1 cDNA of the invention can be isolated based on their homology to the HYDL-1 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the HYDL-1 cDNA of the invention can further be isolated by mapping to the same chromosome or locus as the HYDL-1 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid is at least 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1100, 1100–1200, 1200–1300, 1300 or more nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2× SSC, 0.1% SDS at 50° C., preferably at 55° C., more preferably at 60° C., and even more preferably at 65° C. Ranges intermediate to the above-recited values, e.g., at 60–65° C. or at 55–60° C. are also intended to be encompassed by the present invention. Preferably, an isolated nucleic acid molecule of the invention that hybridizes under stringent conditions to the sequence of SEQ ID NO:1 or 3, and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the HYDL-1 sequences that may exist in the population, the skilled artisan will further appreciate that changes can be introduced by mutation into the nucleotide sequences of SEQ ID NO:1 or 3, thereby leading to changes in the amino acid sequence of the encoded HYDL-1 protein, without altering the functional ability of the HYDL-1 protein. For example, nucleotide substitutions leading to amino acid substitutions at "non-essential" amino acid residues can be made in the sequence of SEQ ID NO:1 or 3. A "non-essential" amino acid residue is a residue that can be altered from the wild-type sequence of HYDL-1 (e.g., the sequence of SEQ ID NO:2) without altering the biological activity, whereas an "essential" amino acid residue is required for biological activity. For example, amino acid residues that are conserved among the HYDL-1 proteins of the present invention, e.g., those present in an alpha/beta hydrolase fold or a catalytic triad, are predicted to be particularly unamenable to alteration. Furthermore, additional amino acid residues that are conserved between the HYDL-1 proteins of the present invention and other members of the HYDL-1 family are not likely to be amenable to alteration.

Accordingly, another aspect of the invention pertains to nucleic acid molecules encoding HYDL-1 proteins that contain changes in amino acid residues that are not essential for activity. Such HYDL-1 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99% or more identical to SEQ ID NO:2.

An isolated nucleic acid molecule encoding an HYDL-1 protein identical to the protein of SEQ ID NO:2 can be created by introducing one or more nucleotide substitutions, additions or deletions into the nucleotide sequence of SEQ ID NO:1 or 3, such that one or more amino acid substitutions, additions or deletions are introduced into the encoded protein. Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an HYDL-1 protein is preferably replaced with another amino acid residue from the same side chain family. Alternatively, in another embodiment, mutations can be introduced randomly along all or part of an HYDL-1 coding sequence, such as by saturation mutagenesis, and the resultant mutants can be screened for HYDL-1 biological activity to identify mutants that retain activity. Following mutagenesis of SEQ ID NO:1 or 3, the encoded protein can be expressed recombinantly and the activity of the protein can be determined.

In a preferred embodiment, a mutant HYDL-1 protein can be assayed for the ability to: 1) modulate the metabolism of biochemical molecules necessary for energy production or storage, 2) modulate the conversion of proproteins and/or prohormones to their active forms; 3) modulate the inactivation of peptides; 4) modulate intra- or intercellular signaling; 5) modulate the biotransformation and detoxification of potentially harmful compounds; and 6) modulate the anabolism and/or catabolism of metabolically important biomolecules.

In addition to the nucleic acid molecules encoding HYDL-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire HYDL-1 coding strand, or to only a portion thereof. In one embodiment, an; antisense nucleic acid molecule is antisense to a "coding region" of the coding strand of a nucleotide sequence encoding HYDL-1. The term "coding region" refers to the region of the nucleotide sequence comprising codons which are translated into amino acid residues (e.g., the coding region of human HYDL-1 corresponds to SEQ ID NO:3). In another embodiment, the antisense nucleic acid molecule is antisense to a "noncoding region" of the coding strand of a nucleotide sequence encoding HYDL-1. The term "noncoding region" refers to 5' and 3' sequences which flank the coding region that are not translated into amino acids (i.e., also referred to as 5' and 3' untranslated regions).

Given the coding strand sequences encoding HYDL-1 disclosed herein (e.g., SEQ ID NO:3), antisense nucleic acids of the invention can be designed according to the rules of Watson and Crick base pairing. The antisense nucleic acid molecule can be complementary to the entire coding region of HYDL-1 mRNA, but more preferably is an oligonucleotide which is antisense to only a portion of the coding or noncoding region of HYDL-1 mRNA. For example, the antisense oligonucleotide can be complementary to the region surrounding the translation start site of HYDL-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an HYDL-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave HYDL-1 mRNA transcripts to thereby inhibit translation of HYDL-1 mRNA. A ribozyme having specificity for an HYDL-1-encoding nucleic acid can be designed based upon the nucleotide sequence of an HYDL-1 cDNA disclosed herein (i.e., SEQ ID NO:1 or 3). For example, a derivative of a Tetrahymena L-19 IVS RNA can be constructed in which the nucleotide sequence of the active site is complementary to the nucleotide sequence to be cleaved in an HYDL-1-encoding mRNA. See, e.g., Cech et al. U.S. Pat. No. 4,987,071; and Cech et al. U.S. Pat. No. 5,116,742. Alternatively, HYDL-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, HYDL-1 gene expression can be inhibited by targeting nucleotide sequences complementary to the regulatory region of the HYDL-1 (e.g., the HYDL-1 promoter and/or enhancers; e.g., nucleotides 1–46 of SEQ ID NO:1) to form triple helical structures that prevent transcription of the HYDL-1 gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12):807–15.

In yet another embodiment, the HYDL-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of HYDL-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of HYDL-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of HYDL-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of HYDL-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous HYDL-1 gene within a cell line or microorganism may be modified by inserting a heterologous DNA regulatory element into the genome of a stable cell line or cloned microorganism such that the inserted regulatory element is operatively linked with the endogenous HYDL-1 gene. For example, an endogenous HYDL-1 gene which is normally "transcriptionally silent", i.e., an HYDL-1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous HYDL-1 gene may be activated by insertion of a promiscuous regulatory element that works across cell types.

A heterologous regulatory element may be inserted into a stable cell line or cloned microorganism, such that it is operatively linked with an endogenous HYDL-1 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated HYDL-1 Proteins and Anti-HYDL-1 Antibodies

One aspect of the invention pertains to isolated HYDL-1 proteins, and biologically active portions thereof, as well as polypeptide fragments suitable for use as immunogens to raise anti-HYDL-1 antibodies. In one embodiment, native HYDL-1 proteins can be isolated from cells or tissue sources by an appropriate purification scheme using standard protein purification techniques. In another embodiment, HYDL-1 proteins are produced by recombinant DNA techniques. Alternative to recombinant expression, an HYDL-1 protein or polypeptide can be synthesized chemically using standard peptide synthesis techniques.

An "isolated" or "purified" protein or biologically active portion thereof is substantially free of cellular material or other contaminating proteins from the cell or tissue source from which the HYDL-1 protein is derived, or substantially free from chemical precursors or other chemicals when chemically synthesized. The language "substantially free of cellular material" includes preparations of HYDL-1 protein in which the protein is separated from cellular components of the cells from which it is isolated or recombinantly produced. In one embodiment, the language "substantially free of cellular material" includes preparations of HYDL-1 protein having less than about 30% (by dry weight) of non-HYDL-1 protein (also referred to herein as a "contaminating protein"), more preferably less than about 20% of non-HYDL-1 protein, still more preferably less than about 10% of non-HYDL-1 protein, and most preferably less than about 5% non-HYDL-1 protein. When the HYDL-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of HYDL-1 protein in which the protein is separated from chemical precursors or other chemicals which are involved in the synthesis of the protein. In one embodiment, the language "substantially free of chemical precursors or other chemicals" includes preparations of HYDL-1 protein having less than about 30% (by dry weight) of chemical precursors or non-HYDL-1 chemicals, more preferably less than about 20% chemical precursors or non-HYDL-1 chemicals, still more preferably less than about 10% chemical precursors or non-HYDL-1 chemicals, and most preferably less than about 5% chemical precursors or non-HYDL-1 chemicals.

As used herein, a "biologically active portion" of an HYDL-1 protein includes a fragment of an HYDL-1 protein which participates in an interaction between an HYDL-1 molecule and a non-HYDL-1 molecule. Biologically active portions of an HYDL-1 protein include peptides comprising amino acid sequences sufficiently identical to or derived from the amino acid sequence of the HYDL-1 protein, e.g., the amino acid sequence shown in SEQ ID NO:2, which include less amino acids than the full length HYDL-1 protein, and exhibit at least one activity of an HYDL-1 protein. Typically, biologically active portions comprise a domain or motif with at least one activity of the HYDL-1 protein, e.g., modulation of cell proliferation and/or migration mechanisms, or metabolism of biochemical molecules. A biologically active portion of an HYDL-1 protein can be a polypeptide which is, for example, 25, 50, 75, 100, 125, 150, 175, 200, 250, 300 or more amino acids in length. Biologically active portions of an HYDL-1 protein can be used as targets for developing agents which modulate an HYDL-1 mediated activity, e.g., cell proliferation and/or migration mechanisms, or metabolism of biochemical molecules.

In one embodiment, a biologically active portion of an HYDL-1 protein comprises at least one alpha/beta hydrolase fold. In another embodiment, a biologically active portion of an HYDL-1 protein of the present invention may contain at least one alpha/beta hydrolase fold and one or more of the following domains: a transmembrane domain, and/or a signal peptide. Moreover, other biologically active portions, in which other regions of the protein are deleted, can be prepared by recombinant techniques and evaluated for one or more of the functional activities of a native HYDL-1 protein.

In a preferred embodiment, the HYDL-1 protein has an amino acid sequence shown in SEQ ID NO:2. In other embodiments, the HYDL-1 protein is substantially identical to SEQ ID NO:2 and retains the functional activity of the protein of SEQ ID NO:2, yet differs in amino acid sequence due to natural allelic variation or mutagenesis, as described in detail in subsection I above. Accordingly, in another embodiment, the HYDL-1 protein is a protein which comprises an amino acid sequence at least about 50%, 55%, 60%, 65%, 70%, 75%, 80%, 85%, 90%, 95%, 96%, 97%, 98%, 99% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the HYDL-1 amino acid sequence of SEQ ID NO:2 having 315 amino acid residues, at least 95, preferably at least 126, more preferably at least 158, even more preferably at least 189, and even more preferably at least 221 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4: 11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to HYDL-1 nucleic acid molecules of the invention. BLAST protein searches can be performed with the XBLAST program, score=100, wordlength=3 to obtain amino acid sequences homologous to HYDL-1 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nl m.nih.gov.

The invention also provides HYDL-1 chimeric or fusion proteins. As used herein, an HYDL-1 "chimeric protein" or "fusion protein" comprises an HYDL-1 polypeptide operatively linked to a non-HYDL-1 polypeptide. An "HYDL-1 polypeptide" refers to a polypeptide having an amino acid sequence corresponding to an HYDL-1 molecule, whereas a "non-HYDL-1 polypeptide" refers to a polypeptide having an amino acid sequence corresponding to a protein which is not substantially homologous to the HYDL-1 protein, e.g., a protein which is different from the HYDL-1 protein and which is derived from the same or a different organism. Within an HYDL-1 fusion protein the HYDL-1 polypeptide can correspond to all or a portion of an HYDL-1 protein. In a preferred embodiment, an HYDL-1 fusion protein comprises at least one biologically active portion of an HYDL-1 protein. In another preferred embodiment, an HYDL-1 fusion protein comprises at least two biologically active portions of an HYDL-1 protein. Within the fusion protein, the term "operatively linked" is intended to indicate that the HYDL-1 polypeptide and the non-HYDL-1 polypeptide are fused in-frame to each other. The non-HYDL-1 polypeptide can be fused to the N-terminus or C-terminus of the HYDL-1 polypeptide.

For example, in one embodiment, the fusion protein is a GST-HYDL-1 fusion protein in which the HYDL-1 sequences are fused to the C-terminus of the GST sequences. Such fusion proteins can facilitate the purification of recombinant HYDL-1.

In another embodiment, the fusion protein is an HYDL-1 protein containing a heterologous signal sequence at its N-terminus. In certain host cells (e.g., mammalian host cells), expression and/or secretion of HYDL-1 can be increased through use of a heterologous signal sequence.

The HYDL-1 fusion proteins of the invention can be incorporated into pharmaceutical compositions and administered to a subject in vivo. The HYDL-1 fusion proteins can be used to affect the bioavailability of an HYDL-1 substrate. Use of HYDL-1 fusion proteins may be useful therapeutically for the treatment of disorders caused by, for example, (i) aberrant modification or mutation of a gene encoding an HYDL-1 protein; (ii) mis-regulation of the HYDL-1 gene; and (iii) aberrant post-translational modification of an HYDL-1 protein.

Moreover, the HYDL-1 fusion proteins of the invention can be used as immunogens to produce anti-HYDL-1 antibodies in a subject, to purify HYDL-1 ligands and in screening assays to identify molecules which inhibit the interaction of HYDL-1 with an HYDL-1 substrate.

Preferably, an HYDL-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An HYDL-1-encoding nucleic acid can be cloned into such an expression vector such that the fusion moiety is linked in-frame to the HYDL-1 protein.

The present invention also pertains to variants of the HYDL-1 proteins which function as either HYDL-1 agonists (mimetics) or as HYDL-1 antagonists. Variants of the HYDL-1 proteins can be generated by mutagenesis, e.g., discrete point mutation or truncation of an HYDL-1 protein. An agonist of the HYDL-1 proteins can retain substantially the same, or a subset, of the biological activities of the naturally occurring form of an HYDL-1 protein. An antagonist of an HYDL-1 protein can inhibit one or more of the activities of the naturally occurring form of the HYDL-1 protein by, for example, competitively modulating an HYDL-1-mediated activity of an HYDL-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the HYDL-1 protein.

In one embodiment, variants of an HYDL-1 protein which function as either HYDL-1 agonists (mimetics) or as HYDL-1 antagonists can be identified by screening combinatorial libraries of mutants, e.g., truncation mutants, of an HYDL-1 protein for HYDL-1 protein agonist or antagonist activity. In one embodiment, a variegated library of HYDL-1 variants is generated by combinatorial mutagenesis at the nucleic acid level and is encoded by a variegated gene library. A variegated library of HYDL-1 variants can be produced by, for example, enzymatically ligating a mixture of synthetic oligonucleotides into gene sequences such that a degenerate set of potential HYDL-1 sequences is expressible as individual polypeptides, or alternatively, as a set of larger fusion proteins (e.g., for phage display) containing the set of HYDL-1 sequences therein. There are a variety of methods which can be used to produce libraries of potential HYDL-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential HYDL-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an HYDL-1 protein coding sequence can be used to generate a variegated population of HYDL-1 fragments for screening and subsequent selection of variants of an HYDL-1 protein. In one embodiment, a library of coding sequence fragments can be generated by treating a double stranded PCR fragment of an HYDL-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the HYDL-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of HYDL-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify HYDL-1 variants (Arkin and Yourvan (1992) *Proc. Natl. Acad. Sci. USA* 89:7811–7815; Delgrave et al. (1993) *Protein Engineering* 6(3): 327–331).

In one embodiment, cell based assays can be exploited to analyze a variegated HYDL-1 library. For example, a library of expression vectors can be transfected into a cell line, e.g., a mammalian cell line, which ordinarily responds to an HYDL-1 ligand in a particular HYDL-1 ligand-dependent manner. The transfected cells are then contacted with an HYDL-1 ligand and the effect of expression of the mutant on, e.g., modulation of cell proliferation and/or migration mechanisms, or HYDL-1 dependent metabolism of biochemical molecules can be detected. Plasmid DNA can then be recovered from the cells which score for inhibition, or alternatively, potentiation of signaling by the HYDL-1 ligand, and the individual clones further characterized.

An isolated HYDL-1 protein, or a portion or fragment thereof, can be used as an immunogen to generate antibodies that bind HYDL-1 using standard techniques for polyclonal and monoclonal antibody preparation. A full-length HYDL-1 protein can be used or, alternatively, the invention provides antigenic peptide fragments of HYDL-1 for use as immunogens. The antigenic peptide of HYDL-1 comprises at least 8 amino acid residues of the amino acid sequence shown in SEQ ID NO:2 and encompasses an epitope of HYDL-1 such that an antibody raised against the peptide forms a specific immune complex with the HYDL-1 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of HYDL-1 that are located on the surface of the protein, e.g., hydrophilic regions, as well as regions with high antigenicity (see, for example, FIG. 2).

An HYDL-1 immunogen typically is used to prepare antibodies by immunizing a suitable subject, (e.g., rabbit, goat, mouse or other mammal) with the immunogen. An appropriate immunogenic preparation can contain, for example, recombinantly expressed HYDL-1 protein or a chemically synthesized HYDL-1 polypeptide. The preparation can further include an adjuvant, such as Freund's complete or incomplete adjuvant, or similar immunostimulatory agent. Immunization of a suitable subject with an immunogenic HYDL-1 preparation induces a polyclonal anti-HYDL-1 antibody response.

Accordingly, another aspect of the invention pertains to anti-HYDL-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as an HYDL-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind HYDL-1 molecules. The term "monoclonal antibody" or "monoclonal antibody composition", as used herein, refers to a population of antibody molecules that contain only one species of an antigen binding site capable of immunoreacting with a particular epitope of HYDL-1. A monoclonal antibody composition thus typically displays a single binding affinity for a particular HYDL-1 protein with which it immunoreacts.

Polyclonal anti-HYDL-1 antibodies can be prepared as described above by immunizing a suitable subject with an HYDL-1 immunogen. The anti-HYDL-1 antibody titer in the immunized subject can be monitored over time by standard techniques, such as with an enzyme linked immunosorbent assay (ELISA) using immobilized HYDL-1. If desired, the antibody molecules directed against HYDL-1 can be isolated from the mammal (e.g., from the blood) and further purified by well known techniques, such as protein A chromatography to obtain the IgG fraction. At an appropriate time after immunization, e.g., when the anti-HYDL-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) Yale *J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an HYDL-1 immunogen as described above, and the culture supernatants of the resulting hybridoma cells are screened to identify a hybridoma producing a monoclonal antibody that binds HYDL-1.

Any of the many well known protocols used for fusing lymphocytes and immortalized cell lines can be applied for the purpose of generating an anti-HYDL-1 monoclonal antibody (see, e.g., G. Galfre et al. (1977) *Nature* 266:55052; Gefter et al. *Somatic Cell Genet.*, cited supra; Lerner, Yale *J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind HYDL-1, e.g., using a standard ELISA assay.

Alternative to preparing monoclonal antibody-secreting hybridomas, a monoclonal anti-HYDL-1 antibody can be identified and isolated by screening a recombinant combinatorial immunoglobulin library (e.g., an antibody phage display library) with HYDL-1 to thereby isolate immunoglobulin library members that bind HYDL-1. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-HYDL-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-HYDL-1 antibody (e.g., monoclonal antibody) can be used to isolate HYDL-1 by standard techniques, such as affinity chromatography or immunoprecipitation. An anti-HYDL-1 antibody can facilitate the purification of natural HYDL-1 from cells and of recombinantly produced HYDL-1 expressed in host cells. Moreover, an anti-HYDL-1 antibody can be used to detect HYDL-1 protein (e.g., in a cellular lysate or cell supernatant) in order to evaluate the abundance and pattern of expression of the HYDL-1 protein. Anti-HYDL-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding an HYDL-1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Meth-* ods in *Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., HYDL-1 proteins, mutant forms of HYDL-1 proteins, fusion proteins, and the like).

The recombinant expression vectors of the invention can be designed for expression of HYDL-1 proteins in prokaryotic or eukaryotic cells. For example, HYDL-1 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in HYDL-1 activity assays, (e.g., direct assays or competitive assays described in detail below), or to generate antibodies specific for HYDL-1 proteins, for example. In a preferred embodiment, an HYDL-1 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS 174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res*. 20:2111–2118). Such alteration of nucleic acid sequences of the invention can be carried out by standard DNA synthesis techniques.

In another embodiment, the HYDL-1 expression vector is a yeast expression vector. Examples of vectors for expression in yeast *S. cerevisiae* include pYepSec1 (Baldari, et al., (1987) *Embo J*. 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, HYDL-1 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol*. 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev*. 1:268–277), lymphoid-specific promoters (Calame and Eaton (1988) *Adv. Immunol*. 43:235–275), in particular promoters of T cell receptors (Winoto and Baltimore (1989) *EMBO J*. 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), lung specific promoters, and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to HYDL-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an HYDL-1 nucleic acid molecule of the invention is introduced, e.g., an HYDL-1 nucleic acid molecule within a recombinant expression vector or an HYDL-1 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an HYDL-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an HYDL-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an HYDL-1 protein. Accordingly, the invention further provides methods for producing an HYDL-1 protein using the host cells of the invention. In one embodiment, the method comprises culturing the host cell of the invention (into which a recombinant expression vector encoding an HYDL-1 protein has been introduced) in a suitable medium such that an HYDL-1 protein is produced. In another embodiment, the method further comprises isolating an HYDL-1 protein from the medium or the host cell.

The host cells of the invention can also be used to produce non-human transgenic animals. For example, in one embodiment, a host cell of the invention is a fertilized oocyte or an embryonic stem cell into which HYDL-1 coding sequences have been introduced. Such host cells can then be used to create non-human transgenic animals in which exogenous HYDL-1 sequences have been introduced into their genome or homologous recombinant animals in which endogenous HYDL-1 sequences have been altered. Such animals are useful for studying the function and/or activity of an HYDL-1 and for identifying and/or evaluating modulators of HYDL-1activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous HYDL-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an HYDL-1-encoding nucleic acid into the male pronuclei of a fertilized oocyte, e.g., by microinjection, retroviral infection, and allowing the oocyte to develop in a pseudopregnant female foster animal. The HYDL-1 cDNA sequence of SEQ ID NO:1 can be introduced as a transgene into the genome of a non-human animal. Alternatively, a nonhuman homologue of a human HYDL-1 gene, such as a mouse or rat HYDL-1 gene, can be used as a transgene. Alternatively, an HYDL-1 gene homologue, such as another HYDL-1 family member, can be isolated based on hybridization to the HYDL-1 cDNA sequences of SEQ ID NO:1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to an HYDL-1 transgene to direct expression of an HYDL-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an HYDL-1 transgene in its genome and/or expression of HYDL-1 MRNA in tissues or cells of the animals. A transgenic founder animal can then be used to breed additional animals carrying the transgene. Moreover, transgenic animals carrying a transgene encoding an HYDL-1 protein can further be bred to other transgenic animals carrying other transgenes.

To create a homologous recombinant animal, a vector is prepared which contains at least a portion of an HYDL-1 gene into which a deletion, addition or substitution has been introduced to thereby alter, e.g., functionally disrupt, the HYDL-1 gene. The HYDL-1 gene can be a human gene (e.g., the cDNA of SEQ ID NO:3), but more preferably, is a non-human homologue of a human HYDL-1 gene (e.g., a cDNA isolated by stringent hybridization with the nucleotide sequence of SEQ ID NO:1). For example, a mouse HYDL-1 gene can be used to construct a homologous recombination nucleic acid molecule, e.g., a vector, suitable for altering an endogenous HYDL-1 gene in the mouse genome. In a preferred embodiment, the homologous recombination nucleic acid molecule is designed such that, upon homologous recombination, the endogenous HYDL-1 gene is functionally disrupted (i.e., no longer encodes a functional protein; also referred to as a "knock out" vector). Alternatively, the homologous recombination nucleic acid molecule can be designed such that, upon homologous recombination, the endogenous HYDL-1 gene is mutated or otherwise altered but still encodes functional protein (e.g., the upstream regulatory region can be altered to thereby alter the expression of the endogenous HYDL-1 protein). In the homologous recombination nucleic acid molecule, the altered portion of the HYDL-1 gene is flanked at its 5' and 3' ends by additional nucleic acid sequence of the HYDL-1 gene to allow for homologous recombination to occur between the exogenous HYDL-1 gene carried by the homologous recombination nucleic acid molecule and an endogenous HYDL-1 gene in a cell, e.g., an embryonic stem cell. The additional flanking HYDL-1 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced HYDL-1 gene has homologously recombined with the endogenous HYDL-1 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The HYDL-1 nucleic acid molecules, fragments of HYDL-1 proteins, and anti-HYDL-1 antibodies (also referred to herein as "active compounds") of the invention can be incorporated into pharmaceutical compositions suitable for administration. Active compounds may include, but are not limited to, peptides, nucleic acids, antibodies, and small inorganic or inorganic compounds. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an HYDL-1 protein or an anti-HYDL-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize-potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of HYDL-1 activity is administered in combination with other agents (e.g., a small molecule), or in conjunction with another, complementary treatment regime. For example, in one embodiment, a modulator of HYDL-1 activity is used to treat a cellular proliferative disorder, e.g., a cancer. Accordingly, modulation of HYDL-1 activity may be used in conjunction with, for example, chemotherapeutic agents and/or anti-angiogenesis agents.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an HYDL-1 protein of the invention has one or more of the following activities: 1) modulation of the metabolism of biochemical molecules necessary for energy production or storage, 2) modulation of the conversion of proproteins and/or prohormones to their active forms; 3) modulation of the inactivation of peptides; 4) modulation of intra- or intercellular signaling; 5) modulation of the biotransformation and detoxification of potentially harmful compounds; and 6) modulation of the anabolism and/or catabolism of metabolically important biomolecules.

The isolated nucleic acid molecules of the invention can be used, for example, to express HYDL-1 protein (e.g., via a recombinant expression vector in a host cell in gene therapy applications), to detect HYDL-1 mRNA (e.g., in a biological sample) or a genetic alteration in an HYDL-1 gene, and to modulate HYDL-1 activity, as described further below. The HYDL-1 proteins can be used to treat disorders characterized by insufficient or excessive production of an HYDL-1 substrate or production of HYDL-1 inhibitors. In addition, the HYDL-1 proteins can be used to screen for naturally occurring HYDL-1 substrates, to screen for drugs or compounds which modulate HYDL-1 activity, as well as to treat disorders characterized by insufficient or excessive production of HYDL-1 protein or production of HYDL-1 protein forms which have decreased, aberrant or unwanted activity compared to HYDL-1 wild type protein (e.g., hydrolase-associated disorders, such as CNS disorders; cardiovascular system disorders; cellular proliferation, growth, differentiation, or migration disorders; hormonal disorders; inflammatory or immune system disorders; hematopoietic or thrombotic disorders; gastrointestinal and digestive disorders; metabolic disorders; hepatic disorders; and renal disorders).

Moreover, the anti-HYDL-1 antibodies of the invention can be used to detect and isolate HYDL-1 proteins, regulate the bioavailability of HYDL-1 proteins, and modulate HYDL-1 activity.

A. Screening Assays

The invention provides a method (also referred to herein as a "screening assay") for identifying modulators, i.e., candidate or test compounds or agents (e.g., peptides, peptidomimetics, small molecules or other drugs) which bind to HYDL-1 proteins, have a stimulatory or inhibitory effect on, for example, HYDL-1 expression or HYDL-1 activity, or have a stimulatory or inhibitory effect on, for example, the expression or activity of an HYDL-1 substrate.

Compounds identified via assays such as those described herein may be useful, for example, for ameliorating an HYDL-1 associated disorder, such as, a cellular proliferative disorder, e.g., cancer. In instances whereby a cellular proliferative disorder results from an overall lower level of HYDL-1 gene expression and/or HYDL-1 protein in a cell or tissue, compounds which accentuate or amplify the expression and/or activity of the HYDL-1 protein may ameliorate symptoms. In other instances, mutations within the HYDL-1 gene may cause aberrant types or excessive amounts of HYDL-1 proteins to be made which have a deleterious effect that leads to a cellular proliferative disease. Similarly, physiological conditions may cause an increase in HYDL-1 gene expression leading to a cellular proliferative disease. In such cases, compounds that inhibit or decrease the expression and/or activity of HYDL-1 may ameliorate symptoms. Assays for testing the effectiveness of compounds identified by techniques are discussed herein.

In one embodiment, the invention provides assays for screening candidate or test compounds which are substrates of an HYDL-1 protein or polypeptide or biologically active portion thereof (e.g., peptides, lipids, or nucleic acids). In another embodiment, the invention provides assays for screening candidate or test compounds which bind to or modulate the activity of an HYDL-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an HYDL-1 protein or biologically active portion thereof is contacted with a test compound and the ability of the test compound to modulate HYDL-1 activity is determined. Determining the ability of the test compound to modulate HYDL-1 activity can be accomplished by monitoring, for example, cell progression through the cell cycle, or the production of one or more specific metabolites in a cell which expresses HYDL-1. The cell, for example, can be of mammalian origin, e.g., an epithelial or neuronal cell. The ability of the test compound to modulate HYDL-1 binding to a substrate (e.g., a peptide, lipid or nucleic acid) or to bind to HYDL-1 can also be determined. Determining the ability of the test compound to modulate HYDL-1 binding to a substrate can be accomplished, for example, by coupling the HYDL-1 substrate with a radioisotope or enzymatic label such that binding of the HYDL-1 substrate to HYDL-1 can be determined by detecting the labeled HYDL-1 substrate in a complex. Alternatively, HYDL-1 could be coupled with a radioisotope or enzymatic label to monitor the ability of a test compound to modulate HYDL-1 binding to an HYDL-1 substrate in a complex. Determining the ability of the test compound to bind HYDL-1 can be accomplished, for example, by coupling the compound with a radioisotope or enzymatic label such that binding of the compound to HYDL-1 can be determined by detecting the labeled compound in a complex. For example, compounds (e.g., HYDL-1 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an HYDL-1 substrate) to interact with HYDL-1 without the labeling of any of the interactants. For example, a microphysiometer can be used to detect the interaction of a compound with HYDL-1 without the labeling of either the compound or the HYDL-1. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and HYDL-1.

In another embodiment, an assay is a cell-based assay comprising contacting a cell expressing an HYDL-1 target molecule (e.g., an HYDL-1 substrate) with a test compound and determining the ability of the test compound to modulate (e.g., stimulate or inhibit) the activity of the HYDL-1 target molecule. Determining the ability of the test compound to modulate the activity of an HYDL-1 target molecule can be accomplished, for example, by determining the ability of the HYDL-1 protein to bind to or interact with the HYDL-1 target molecule.

Determining the ability of the HYDL-1 protein, or a biologically active fragment thereof, to bind to or interact with an HYDL-1 target molecule can be accomplished by one of the methods described above for determining direct binding. In a preferred embodiment, determining the ability of the HYDL-1 protein to bind to or interact with an HYDL-1 target molecule can be accomplished by determining the activity of the target molecule. For example, the activity of the target molecule can be determined by detecting induction of a cellular response (i.e., cell proliferation, migration and/or metabolic activity), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which an HYDL-1 protein or biologically active portion thereof is contacted with a test compound and the ability of the test compound to bind to the HYDL-1 protein or biologically active portion thereof is determined. Preferred biologically active portions of the HYDL-1 proteins to be used in assays of the present invention include fragments which participate in interactions with non-HYDL-1 molecules, e.g., fragments with high surface probability scores (see, for example, FIG. 2). Binding of the test compound to the HYDL-1 protein can be determined either directly or indirectly as described above. In a preferred embodiment, the assay includes contacting the HYDL-1 protein or biologically active portion thereof with a known compound which binds HYDL-1 to form an assay mixture, contacting the assay mixture with a test compound, and determining the ability of the test compound to interact with an HYDL-1 protein, wherein determining the ability of the test compound to interact with an HYDL-1 protein comprises determining the ability of the test compound to preferentially bind to HYDL-1 or biologically active portion thereof as compared to the known compound.

In another embodiment, the assay is a cell-free assay in which an HYDL-1 protein or biologically active portion thereof is contacted with a test compound and the ability of the test compound to modulate (e.g., stimulate or inhibit) the activity of the HYDL-1 protein or biologically active portion thereof is determined. Determining the ability of the test compound to modulate the activity of an HYDL-1 protein can be accomplished, for example, by determining the ability of the HYDL-1 protein to bind to an HYDL-1 target molecule by one of the methods described above for determining direct binding. Determining the ability of the HYDL-1 protein to bind to an HYDL-1 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an HYDL-1 protein can be accomplished by determining the ability of the HYDL-1 protein to further modulate the activity of a downstream effector of an HYDL-1 target molecule. For example, the activity of the effector molecule on an appropriate target can be determined or the binding of the effector to an appropriate target can be determined as previously described.

In yet another embodiment, the cell-free assay involves contacting an HYDL-1 protein or biologically active portion thereof with a known compound (e.g., an HYDL-1 substrate) which binds the HYDL-1 protein to form an assay mixture, contacting the assay mixture with a test compound, and determining the ability of the test compound to interact with the HYDL-1 protein, wherein determining the ability of the test compound to interact with the HYDL-1 protein comprises determining the ability of the HYDL-1 protein to preferentially bind to or modulate the activity of an HYDL-1 target protein, e.g., catalyze the cleavage, e.g., the hydrolytic cleavage, of a chemical bond within the target protein.

In more than one embodiment of the above assay methods of the present invention, it may be desirable to immobilize either HYDL-1 or its target molecule to facilitate separation of complexed from uncomplexed forms of one or both of the proteins, as well as to accommodate automation of the assay. Binding of a test compound to an HYDL-1 protein, or interaction of an HYDL-1 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/HYDL-1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or HYDL-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of HYDL-1 binding or activity determined using standard techniques.

Other techniques for immobilizing proteins on matrices can also be used in the screening assays of the invention. For example, either an HYDL-1 protein or an HYDL-1 target molecule can be immobilized utilizing conjugation of biotin and streptavidin. Biotinylated HYDL-1 protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with HYDL-1 protein or target molecules but which do not interfere with binding of the HYDL-1 protein to its target molecule can be derivatized to the wells of the plate, and unbound target or HYDL-1 protein trapped in the wells by antibody conjugation. Methods for detecting such complexes, in addition to those described above for the GST-immobilized complexes, include immunodetection of complexes using antibodies reactive with the HYDL-1 protein or target molecule, as well as enzyme-linked assays which rely on detecting an enzymatic activity associated with the HYDL-1 protein or target molecule.

In another embodiment, modulators of HYDL-1 expression are identified in a method wherein a cell is contacted with a candidate compound and the expression of HYDL-1 mRNA or protein in the cell is determined. The level of expression of HYDL-1 mRNA or protein in the presence of the candidate compound is compared to the level of expression of HYDL-1 mRNA or protein in the absence of the candidate compound. The candidate compound can then be identified as a modulator of HYDL-1 expression based on this comparison. For example, when expression of HYDL-1 mRNA or protein is greater (statistically significantly greater) in the presence of the candidate compound than in its absence, the candidate compound is identified as a stimulator of HYDL-1 mRNA or protein expression. Alternatively, when expression of HYDL-1 MRNA or protein is less (statistically significantly less) in the presence of the candidate compound than in its absence, the candidate compound is identified as an inhibitor of HYDL-1 mRNA or protein expression. The level of HYDL-1 mRNA or protein expression in the cells can be determined by methods described herein for detecting HYDL-1 mRNA or protein.

In yet another aspect of the invention, the HYDL-1 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with HYDL-1 ("HYDL-1 binding proteins" or "HYDL-1-bp") and are involved in HYDL-1 activity. Such HYDL-1 binding proteins are also likely to be involved in the propagation of signals by the HYDL-1 proteins or HYDL-1 targets as, for example, downstream elements of an HYDL-1-mediated signaling pathway. Alternatively, such HYDL-1 binding proteins are likely to be HYDL-1 inhibitors.

The two-hybrid system is based on the modular nature of most transcription factors, which consist of separable DNA-binding and activation domains. Briefly, the assay utilizes two different DNA constructs. In one construct, the gene that codes for an HYDL-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an HYDL-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the HYDL-1 protein.

In another aspect, the invention pertains to a combination of two or more of the assays described herein. For example, a modulating agent can be identified using a cell-based or a cell free assay, and the ability of the agent to modulate the activity of an HYDL-1 protein can be confirmed in vivo, e.g., in an animal such as an animal model for cellular transformation and/or tumorigenesis, or an animal model for a metabolic disorder.

This invention further pertains to novel agents identified by the above-described screening assays. Accordingly, it is within the scope of this invention to further use an agent identified as described herein in an appropriate animal model. For example, an agent identified as described herein (e.g., an HYDL-1 modulating agent, an antisense HYDL-1 nucleic acid molecule, an HYDL-1-specific antibody, or an HYDL-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate symptoms of, for example, a cellular proliferative disorder. Cell-based and animal model-based assays for the identification of compounds exhibiting an ability to ameliorate the symptoms of a cellular proliferative disorder are described herein.

In one aspect, cell-based systems, as described herein, may be used to identify compounds which may act to ameliorate symptoms of a cellular proliferative disorder. For example, such cell systems may be exposed to a test compound (e.g., suspected of exhibiting an ability to ameliorate symptoms of a cellular proliferative disorder), at a sufficient concentration and for a time sufficient to elicit amelioration of symptoms of a cellular proliferative disorder in the exposed cells. After exposure, the cells are examined to determine whether one or more of the cellular phenotypes associated with a cellular proliferative disorder has been altered to resemble a normal or wild type, non-cellular proliferative disorder phenotype. Cellular phenotypes that are associated with cellular proliferative disorders include aberrant proliferation and migration, anchorage independent growth, and loss of contact inhibition.

In addition, animal-based models of cellular proliferative disorders, such as those described herein, may be used to identify compounds capable of ameliorating symptoms of a cellular proliferative disorder. Such animal models may be used as test substrates for the identification of drugs, pharmaceuticals, therapies, and interventions which may be effective in treating a cellular proliferative disorder. For example, animal models may be exposed to a test compound at a sufficient concentration and for a time sufficient to ameliorate symptoms of a cellular proliferative disorder in the exposed animals. The response of the animals to the exposure may be monitored by assessing amelioration of symptoms of a cellular proliferative disorder, for example, reduction in tumor size, invasive and/or metastatic potential, as well as tumor burden, before and after treatment.

With regard to intervention, any treatments which reverse any aspect of a cellular proliferative disorder should be considered as candidates for human disease therapeutic intervention. Dosages of test agents may be determined by deriving dose-response curves.

Additionally, gene expression patterns may be utilized to assess the ability of a compound to ameliorate symptoms of a cellular proliferative disorder. For example, the expression pattern of one or more genes may form part of a "gene expression profile" or "transcriptional profile" which may be then in such an assessment. "Gene expression profile" or "transcriptional profile", as used herein, includes the pattern of mRNA expression obtained for a given tissue or cell type under a given set of conditions. Such conditions may include, but are not limited to, cell proliferation, differentiation, transformation, tumorigenesis and metastasis. Gene expression profiles may be generated, for example, by utilizing a differential display procedure, Northern analysis and/or RT-PCR. In one embodiment, HYDL-1 gene sequences may be used as probes and/or PCR primers for the generation and corroboration of such gene expression profiles.

Gene expression profiles may be characterized for known states, for example, a tumorigenic/disease state or normal state, within the cell- and/or animal-based model systems. Subsequently, these known gene expression profiles may be compared to ascertain the effect of a test compound on modifying such gene expression profiles.

For example, administration of a test compound may cause the gene expression profile of a cellular proliferative disorder model system to more closely resemble the control system. Administration of a test compound may, alternatively, cause the gene expression profile of a control system to begin to mimic a cellular proliferative disorder state. Such a test compound may, for example, be used in further characterizing the test compound of interest, or may be used in the generation of additional animal models.

Cells that contain and express HYDL-1 gene sequences which encode an HYDL-1 protein, and further, exhibit cellular phenotypes associated with a cellular proliferative disorder, may be used to identify compounds that exhibit cellular growth modulatory activity. Such cells include tumor cell lines, such as those exemplified herein, as well as generic mammalian cell lines such as COS cells. Further, such cells may include recombinant cell lines derived from a transgenic animal. For example, animal models of tumorigenesis, such as those discussed above, may be used to generate cell lines that can be used as cell culture models for this disorder. While primary cultures derived from transgenic animals may be utilized, the generation of continuous cell lines is preferred. For examples of techniques which may be used to derive a continuous cell line from the transgenic animals, see Small et al., (1985) *Mol. Cell Biol.* 5:642–648.

Alternatively, cells of a cell type known to be involved in cellular proliferative disorder may be transfected with sequences capable of increasing or decreasing the amount of HYDL-1 gene expression within the cell. For example, HYDL-1 gene sequences may be introduced into, and overexpressed in, the genome of the cell of interest, or, if endogenous HYDL-1 gene sequences are present, they may be either overexpressed or, alternatively, disrupted in order to underexpress or inactivate HYDL-1 gene expression.

In order to overexpress an HYDL-1 gene, the coding portion of the HYDL-1 gene may be ligated to a regulatory sequence which is capable of driving gene expression in the cell type of interest. Such regulatory regions will be well known to those of skill in the art, and may be utilized in the absence of undue experimentation. Recombinant methods for expressing target genes are described above.

For underexpression of an endogenous HYDL-1 gene sequence, such a sequence may be isolated and engineered such that when reintroduced into the genome of the cell type of interest, the endogenous HYDL-1 alleles will be inactivated. Preferably, the engineered HYDL-1 sequence is introduced via gene targeting such that the endogenous HYDL-1 sequence is disrupted upon integration of the engineered HYDL-1 sequence into the cell's genome. Transfection of host cells with HYDL-1 genes is discussed, above.

Cells treated with test compounds or transfected with HYDL-1 genes can be examined for phenotypes associated with a cellular proliferative disorder, e.g., dysregulated proliferation and migration, anchorage independent growth, and loss of contact inhibition.

Transfection of an HYDL-1 nucleic acid may be accomplished by using standard techniques (described herein and in, for example, Ausubel (1989) supra). Transfected cells should be evaluated for the presence of the recombinant HYDL-1 gene sequences, for expression and accumulation of HYDL-1 mRNA, and for the presence of recombinant HYDL-1 protein production. In instances wherein a decrease in HYDL-1 gene expression is desired, standard techniques may be used to demonstrate whether a decrease in endogenous HYDL-1 gene expression and/or in HYDL-1 protein production is achieved.

Cellular models for the study of cellular proliferative disorder are known in the art, and include cell lines derived from clinical tumors, cells exposed to carcinogenic agents, and cell lines with genetic alterations in growth regulatory genes, for example, oncogenes (e.g., ras) and tumor suppressor genes (e.g., p53).

Animal based models of cellular proliferative diseases, e.g., tumorigenesis, are well known in the art, and include, for example, non-recombinant and engineered transgenic animals. Models for studying tumorigenesis in vivo include carcinogen-induced tumors, injection and/or transplantation of tumor cells into an animal, as well as animals bearing mutations in growth regulatory genes.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the HYDL-1 nucleotide sequences, described herein, can be used to map the location of the HYDL-1 genes on a chromosome. The mapping of the HYDL-1 sequences to chromosomes is an important first step in correlating these sequences with genes associated with disease.

Briefly, HYDL-1 genes can be mapped to chromosomes by preparing PCR primers (preferably 15–25 bp in length) from the HYDL-1 nucleotide sequences. Computer analysis of the HYDL-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the HYDL-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the HYDL-1 nucleotide sequences to design oligonucleotide primers, sublocalization can be achieved with panels of fragments from specific chromosomes. Other mapping strategies which can similarly be used to map an HYDL-1 sequence to its chromosome include in situ hybridization (described in Fan, Y. et al. (1990) *Proc. Natl. Acad. Sci. USA*, 87:6223–27), prescreening with labeled flow-sorted chromosomes, and preselection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the HYDL-1 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The HYDL-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the HYDL-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The HYDL-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from HYDL-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of HYDL-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic. identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the HYDL-1 nucleotide sequences or portions thereof, e.g., fragments derived from the noncoding regions of SEQ ID NO:1 having a length of at least 20 bases, preferably at least 30 bases.

The HYDL-1 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such HYDL-1 probes can be used to identify tissue by species and/or by organ type.

In a similar fashion, these reagents, e.g., HYDL-1 primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining HYDL-1 protein and/or nucleic acid expression as well as HYDL-1 activity, in the context of a biological sample (e.g., blood, serum, cells, tissue) to thereby determine whether an individual is afflicted with a disease or disorder, or is at risk of developing a disorder, associated with aberrant or unwanted HYDL-1 expression or activity, e.g., a cellular proliferative disorder. The invention also provides for prognostic (or predictive) assays for determining whether an individual is at risk of developing a disorder associated with HYDL-1 protein, nucleic acid expression or activity. For example, mutations in an HYDL-1 gene can be assayed in a biological sample. Such assays can be used for prognostic or predictive purpose to thereby phophylactically treat an individual prior to the onset of a disorder characterized by or associated with HYDL-1 protein, nucleic acid expression or activity.

Another aspect of the invention pertains to monitoring the influence of agents (e.g., drugs, compounds) on the expression or activity of HYDL-1 in clinical trials.

These and other agents are described in further detail in the following sections.

1. Diagnostic Assays

An exemplary method for detecting the presence or absence of HYDL-1 protein or nucleic acid in a biological sample involves obtaining a biological sample from a test subject and contacting the biological sample with a compound or an agent capable of detecting HYDL-1 protein or nucleic acid (e.g.,. mRNA, or genomic DNA) that encodes HYDL-1 protein such that the presence of HYDL-1 protein or nucleic acid is detected in the biological sample. A preferred agent for detecting HYDL-1 mRNA or genomic DNA is a labeled nucleic acid probe capable of hybridizing to HYDL-1 mRNA or genomic DNA. The nucleic acid probe can be, for example, the HYDL-1 nucleic acid set forth in SEQ ID NO:1 or 3, or a portion thereof, such as an oligonucleotide of at least 15, 30, 50, 100, 250 or 500 nucleotides in length and sufficient to specifically hybridize under stringent conditions to HYDL-1 mRNA or genomic DNA. Other suitable probes for use in the diagnostic assays of the invention are described herein.

A preferred agent for detecting HYDL-1 protein is an antibody capable of binding to HYDL-1 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect HYDL-1 mRNA, protein, or genomic DNA in a biological sample in vitro as well as in vivo. For example, in vitro techniques for detection of HYDL-1 mRNA include Northern hybridizations and in situ hybridizations. In vitro techniques for detection of HYDL-1 protein include enzyme linked immunosorbent assays (ELISAs), Western blots, immunoprecipitations and immunofluorescence. In vitro techniques for detection of HYDL-1 genomic DNA include Southern hybridizations. Furthermore, in vivo techniques for detection of HYDL-1 protein include introducing into a subject a labeled anti-HYDL-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting HYDL-1 protein, mRNA, or genomic DNA, such that the presence of HYDL-1 protein, mRNA or genomic DNA is detected in the biological sample, and comparing the presence of HYDL-1 protein, mRNA or genomic DNA in the control sample with the presence of HYDL-1 protein, mRNA or genomic DNA in the test sample.

The invention also encompasses kits for detecting the presence of HYDL-1 in a biological sample. For example, the kit can comprise a labeled compound or agent capable of detecting HYD-1L protein or mRNA in a biological sample; means for determining the amount of HYDL-1 in the sample; and means for comparing the amount of HYDL-1 in the sample with a standard. The compound or agent can be packaged in a suitable container. The kit can further comprise instructions for using the kit to detect HYDL-1 protein or nucleic acid.

2. Prognostic Assays

The diagnostic methods described herein can furthermore be utilized to identify subjects having or at risk of developing a disease or disorder associated with aberrant or unwanted HYDL-1 expression or activity, e.g., a cellular proliferative disorder. As used herein, the term "aberrant" includes a HYDL-1 expression or activity which deviates from the wild type HYDL-1 expression or activity. Aberrant expression or activity includes increased or decreased expression or activity, as well as expression or activity which does not follow the wild type developmental pattern of expression or the subcellular pattern of expression. For example, aberrant HYDL-1 expression or activity is intended to include the cases in which a mutation in the HYDL-1 gene causes the HYDL-1 gene to be under-expressed or over-expressed and situations in which such mutations result in a non-functional HYDL-1 protein or a protein which does not function in a wild-type fashion, e.g., a protein which does not interact with a HYDL-1 substrate, or one which interacts with a non-HYDL-1 substrate. As used herein, the term "unwanted" includes an unwanted phenomenon involved in a biological response such as cellular proliferation. For example, the term unwanted includes a HYDL-1 expression or activity which is undesirable in a subject.

The assays described herein, such as the preceding diagnostic assays or the following assays, can be utilized to identify a subject having or at risk of developing a disorder associated with a misregulation in HYDL-1 protein activity or nucleic acid expression, such as a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. Alternatively, the prognostic assays can be utilized to identify a subject having or at risk for developing a disorder associated with a misregulation in HYDL-1 protein activity or nucleic acid expression, such as a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. Thus, the present invention provides a method for identifying a disease or disorder associated with aberrant or unwanted HYDL-1 expression or activity in which a test sample is obtained from a subject and HYDL-1 protein or nucleic acid (e.g., mRNA or genomic DNA) is detected, wherein the presence of HYDL-1 protein or nucleic acid. is diagnostic for a subject having or at risk of developing a disease or disorder associated with aberrant or unwanted HYDL-1 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted HYDL-1 expression or activity. For example, such methods can be used to determine whether a subject can be effectively treated with an agent for a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. Thus, the present invention provides methods for determining whether a subject can be effectively treated with an agent for a disorder associated with aberrant or unwanted HYDL-1 expression or activity in which a test sample is obtained and HYDL-1 protein or nucleic acid expression or activity is detected (e.g., wherein the abundance of HYDL-1protein or nucleic acid expression or activity is diagnostic for a subject that can be administered the agent to treat a disorder associated with aberrant or unwanted HYDL-1 expression or activity).

The methods of the invention can also be used to detect genetic alterations in an HYDL-1 gene, thereby determining if a subject with the altered gene is at risk for a disorder characterized by misregulation in HYDL-1 protein activity or nucleic acid expression, such as a CNS disorder, a cardiovascular disorder, a muscular disorder, a hormonal disorder, a gastrointestinal disorder, an inflammatory or immune system disorder, or a cell proliferation, growth, differentiation, or migration disorder. In preferred embodiments, the methods include detecting, in a sample of cells from the subject, the presence or absence of a genetic alteration characterized by at least one of an alteration affecting the integrity of a gene encoding an HYDL-1 protein, or the mis-expression of the HYDL-1 gene. For example, such genetic alterations can be detected by ascertaining the existence of at least one of 1) a deletion of one or more nucleotides from an HYDL-1 gene; 2) an addition of one or more nucleotides to an HYDL-1 gene; 3) a substitution of one or more nucleotides of an HYDL-1 gene, 4) a chromosomal rearrangement of an HYDL-1 gene; 5) an alteration in the level of a messenger RNA transcript of an HYDL-1 gene, 6) aberrant modification of an HYDL-1 gene, such as of the methylation pattern of the genomic DNA, 7) the presence of a non-wild type splicing pattern of a messenger RNA transcript of an HYDL-1 gene, 8) a non-wild type level of an HYDL-1 protein, 9) allelic loss of an HYDL-1 gene, and 10) inappropriate post-translational modification of an HYDL-1 protein. As described herein, there are a large number of assays known in the art which can be used for detecting alterations in an HYDL-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683.202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in an HYDL-1 gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an HYDL-1 gene under conditions such that hybridization and amplification of the HYDL-1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an HYDL-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in HYDL-1 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in HYDL-1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the HYDL-1 gene and detect mutations by comparing the sequence of the sample HYDL-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the HYDL-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type HYDL-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in HYDL-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an HYDL-1 sequence, e.g., a wild-type HYDL-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in HYDL-1 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control HYDL-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an HYDL-1 gene.

Furthermore, any cell type or tissue in which HYDL-1 is expressed may be utilized in the prognostic assays described herein.

3. Monitoring of Effects During Clinical Trials

Monitoring the influence of agents (eg., drugs) on the expression or activity of an HYDL-1 protein (e.g., the modulation of cell proliferation and/or migration) can be applied not only in basic drug screening, but also in clinical trials. For example, the effectiveness of an agent determined by a screening assay as described herein to increase HYDL-1 gene expression, protein levels, or upregulate HYDL-1 activity, can be monitored in clinical trials of subjects exhibiting decreased HYDL-1 gene expression, protein levels, or downregulated HYDL-1 activity. Alternatively, the effectiveness of an agent determined by a screening assay to decrease HYDL-1 gene expression, protein levels, or downregulate HYDL-1 activity, can be monitored in clinical trials of subjects exhibiting increased HYDL-1 gene expression, protein levels, or upregulated HYDL-1 activity. In such clinical trials, the expression or activity of an HYDL-1 gene, and preferably, other genes that have been implicated in, for example, an HYDL-1-associated disorder can be used as a "read out" or markers of the phenotype of a particular cell.

For example, and not by way of limitation, genes, including HYDL-1, that are modulated in cells by treatment with an agent (e.g., compound, drug or small molecule) which modulates HYDL-1 activity (e.g., identified in a screening assay as described herein) can be identified. Thus, to study the effect of agents on HYDL-1-associated disorders (e.g., disorders characterized by deregulated cell proliferation and/or migration), for example, in a clinical trial, cells can be isolated and RNA prepared and analyzed for the levels of expression of HYDL-1 and other genes implicated in the HYDL-1-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of HYDL-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an HYDL-1 protein, mRNA, or genomic DNA in the preadministration sample; (iii) obtaining one or more post-administration samples from the subject; (iv) detecting the level of expression or activity of the HYDL-1 protein, mRNA, or genomic DNA in the post-administration samples; (v) comparing the level of expression or activity of the HYDL-1 protein, mRNA, or genomic DNA in the pre-administration sample with the HYDL-1 protein, mRNA, or genomic DNA in the post administration sample or samples; and (vi) altering the administration of the agent to the subject accordingly. For example, increased administration of the agent may be desirable to increase the expression or activity of HYDL-1 to higher levels than detected, i.e., to increase the effectiveness of the agent. Alternatively, decreased administration of the agent may be desirable to decrease expression or activity of HYDL-1 to lower levels than detected, i.e. to decrease the effectiveness of the agent. According to such an embodiment, HYDL-1 expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder or having a disorder associated with aberrant or unwanted HYDL-1 expression or activity, e.g., a hydrolase-associated disorder such as a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the HYDL-1 molecules of the present invention or HYDL-1modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted HYDL-1 expression or activity, by administering to the subject an HYDL-1 or an agent which modulates HYDL-1 expression or at least one HYDL-1 activity. Subjects at risk for a disease which is caused or contributed to by aberrant or unwanted HYDL-1 expression or activity can be identified by, for example, any or a combination of diagnostic or prognostic assays as described herein. Administration of a prophylactic agent can occur prior to the manifestation of symptoms characteristic of the HYDL-1 aberrancy, such that a disease or disorder is prevented or, alternatively, delayed in its progression. Depending on the type of HYDL-1 aberrancy, for example, an HYDL-1, HYDL-1 agonist or HYDL-1 antagonist agent can be used for treating the subject. The appropriate agent can be determined based on screening assays described herein.

2. Therapeutic Methods

Another aspect of the invention pertains to methods of modulating HYDL-1 expression or activity for therapeutic purposes. Accordingly, in an exemplary embodiment, the modulatory method of the invention involves contacting a cell with an HYDL-1 or agent that modulates one or more of the activities of HYDL-1 protein activity associated with the cell. An agent that modulates HYDL-1 protein activity can be an agent as described herein, such as a nucleic acid or a protein, a naturally-occurring target molecule of an HYDL-1 protein (e.g., an HYDL-1 substrate), an HYDL-1 antibody, an HYDL-1 agonist or antagonist, a peptidomimetic of an HYDL-1 agonist or antagonist, or other small molecule. In one embodiment, the agent stimulates one or more HYDL-1 activities. Examples of such stimulatory agents include active HYDL-1 protein and a nucleic acid molecule encoding HYDL-1 that has been introduced into the cell. In another embodiment, the agent inhibits one or more HYDL-1 activities. Examples of such inhibitory agents include antisense HYDL-1 nucleic acid molecules, anti-HYDL-1 antibodies, and HYDL-1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an HYDL-1 protein or nucleic acid molecule. In one embodiment, the method involves administering an agent (e.g., an agent identified by a screening assay described herein), or combination of agents that modulates (e.g., upregulates or downregulates) HYDL-1 expression or activity. In another embodiment, the method involves administering an HYDL-1 protein or nucleic acid molecule as therapy to compensate for reduced, aberrant, or unwanted HYDL-1 expression or activity.

Stimulation of HYDL-1 activity is desirable in situations in which HYDL-1 is abnormally downregulated and/or in which increased HYDL-1 activity is likely to have a beneficial effect. Likewise, inhibition of HYDL-1 activity is desirable in situations in which HYDL-1 is abnormally upregulated and/or in which decreased HYDL-1 activity is likely to have a beneficial effect.

3. Pharmacogenomics

The HYDL-1 molecules of the present invention, as well as agents, or modulators which have a stimulatory or inhibitory effect on HYDL-1 activity (e.g., HYDL-1 gene expression) as identified by a screening assay described herein can be administered to individuals to treat (prophylactically or therapeutically) HYDL-1-associated disorders (e.g., CNS disorders, cardiovascular disorders, muscular disorders, hormonal disorders, gastrointestinal disorders, metabolic disorders, inflammatory or immune system disorders, or cell proliferation, growth, differentiation, or migration disorders) associated with aberrant or unwanted HYDL-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an HYDL-1 molecule or HYDL-1 modulator as well as tailoring the dosage and/or therapeutic regimen of treatment with an HYDL-1 molecule or HYDL-1 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–1): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a HYDL-1 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an HYDL-1 molecule or HYDL-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an HYDL-1 molecule or HYDL-1 modulator, such as a modulator identified by one of the exemplary screening assays described herein.

This invention is further illustrated by the following examples which should not be construed as limiting. The contents of all references, patents and published patent applications cited throughout this application, as well as the Figures, are incorporated herein by reference.

EXAMPLES

Example 1

Identification and Characterization of Human HYDL-1 cDNA

In this example, the identification and characterization of the gene encoding human HYDL-1 (clone Fbh33167F11) is described.

Isolation of the HYDL-1 cDNA

The invention is based, at least in part, on the discovery of a human gene encoding a novel protein, referred to herein as HYDL-1. The entire sequence of human clone Fbh33167F11 was determined and found to contain an open reading frame termed human "HYDL-1."

The nucleotide sequence encoding the human HYDL-1 protein is shown in FIG. 1 and is set forth as SEQ ID NO:1. The protein encoded by this nucleic acid comprises about 315 amino acids and has the amino acid sequence shown in FIG. I and set forth as SEQ ID NO:2. The coding region (open reading frame) of SEQ ID NO:1 is set forth as SEQ ID NO:3.

Analysis of the Human HYDL-1 Molecules

The amino acid sequences of human HYDL-1 was analyzed using the program PSORT (http://www.psort.nibb.ac.jp) to predict the localization of the proteins within the cell. This program assesses the presence of different targeting and localization amino acid sequences within the query sequence. The results of the analyses show that human HYDL-1 (SEQ ID NO:2) may be localized to the mitochondria, to the cytoplasm, to the nucleus, or to peroxisomes. In a preferred embodiment, the HYDL-1 protein is localized to the mitochondria.

The amino acid sequence of HYDL-1 was analyzed by the SignalP program (Henrik, et al. (1997) *Protein Engineering* 10:1–6) for the presence of a signal peptide. This analysis revealed the possible presence of a signal peptide in the amino acid sequence of HYDL-1 from residues 1–16.

Searches of the amino acid sequence of HYDL-1 was performed against the Memsat database (FIG. 3). These searches resulted in the identification of two transmembrane domains in the amino acid sequence of human HYDL-1 (SEQ ID NO:2) at about residues 130–152 and 255–271.

A search was also performed against the Prosite database, and resulted in the identification of several possible phosphorylation sites within the human HYDL-1 protein. Protein kinase C phosphorylation sites were identified at residues 56–58 and 93–95, and a casein kinase II phosphorylation site was identified at residues 167–170 of human HYDL-1. The search also identified the presence of N-myristoylation site motifs at amino acid residues 4–9, 43–48, 74–79, 131–136, and 143–148 of human HYDL-1. In addition, the search identified an amidation site at amino acid residues 93–96, and an ATP/GTP-binding site motif A (P-loop) at amino acid residues 139–146 of human HYDL-1.

A search of the amino acid sequence of HYDL-1 was also performed against the HMM database (FIG. 4). This search resulted in the identification of an "alpha/beta hydrolase fold" in the amino acid sequence of HYDL-1 (SEQ ID NO:2) at about residues 95–314 (score=83.1). This search also resulted in the identification of a "thioesterase" domain at about residues 67–287 of SEQ ID NO:2, and a lipase_3 domain at about residues 75–247 of SEQ ID NO:2.

A BLASTP 2.0MP-WashU search (Altschul et al. (1990) *J. Mol. Biol.* 215:403) of the amino acid sequence of HYDL-1 revealed local sequence identity between HYDL-1 (SEQ ID NO:2) and *C. elegans* (Z81105) similar to alpha/beta hydrolase fold (Accession No. CAB03219), the *Drosophila melanogaster* CG2059 gene product (Accession No. AAF46249, the Y193_HAEIN putative esterase/lipase HI0193 (Accession No. Q57427), the YBFF_ECOLI putative esterase/lipase YBFF (Accession No. P75736), the YGIL_YEASR hypothetical 38.5 KDa protein in ERV1-GLS2 intergenic region (Accession No. P53219), and *Schizosaccharomyces pombe* hypothetical alpha/beta hydrolase fold domain protein (Accession No. CAA22555). FIG. 5 depicts a multiple sequence alignment of human HYDL-1 with other proteins containing an alpha/beta hydrolase fold.

A search of the amino acid sequence of HYDL-1 was also performed against the ProDom database (FIG. 6). This search resulted in the local alignment of the human HYDL-1 protein with p99.2 (1) P71702_MYCTU (hypothetical 32.1 Kd protein CY21D4.08C hypothetical protein) over amino acid residues 67–314 [score=173]. This search also resulted in the local alignment of HYDL-1 with p99.2 (304) PIP (9) PRXC (6) LIP (6) (protein hydrolase transferase putative esterase biosynthesis epoxide acyltransferase lipase synthase) over amino acid residues 259–315 [score=82], over amino acid residues 96–217 [score=79], and over amino acid residues 261–314 [score=44]. In addition, this search resulted in the local alignment of HYDL-1 with p99.2 (2) P76932(1) YFBB (1) (of similar from bases section the complete genome protein MEND-MENB) over amino acid residues 62–153 [score=89]; with p99.2 (1) O54172_STRCO (hydrolase hyrdrolase) over amino acid residues 55–173 [score=81]; and with p99.2 (1) O86608_STRCO (3-oxoadipate enol-lactone hydrolase/4-carboxymuconolactone decarboxylase hydrolase) over amino acid residues 55–196 [score=74].

Example 2

Regulation of HYDL-1 Expression During the Cell Cycle

Cultures of MCF10A cells were synchronized with 300 μM mimosine for 18–19 hours. The mimosine was then removed (0 hour) and cells were harvested every 3 hours over a 24 hour period. FACS analysis demonstrated that approximately 85% of the cell population was synchronized in G0/G1. After 9 hours, >40% of the cell population had shifted into G2/M.

Figure 7:
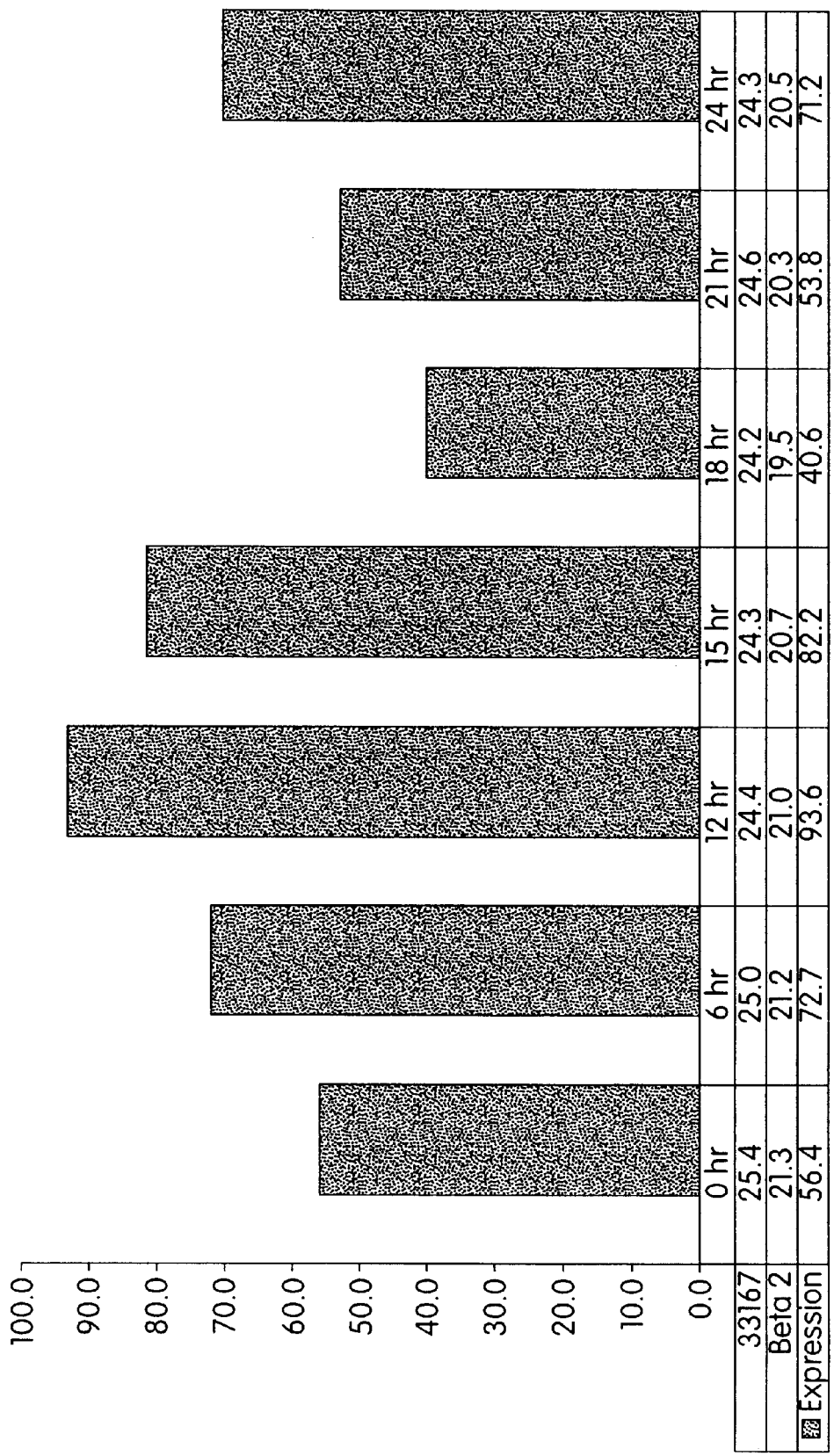
FIG. 7 is a graph depicting the results of a RT-PCR analysis of HYDL-1expression in synchronized MCF10A cells.

The expression of HYDL-1 in synchronized cells was assessed by PCR analysis. As shown in FIG. 7, HYDL-1 expression was increased 6–15 hours following the removal of mimosine. These data demonstrate that HYDL-1 expression is regulated in the S/G2/M phases of the cell cycle in MCF10A cells.

Example 3

HYDL-1 Expression in Human Tumor Cells

Figure 8A:
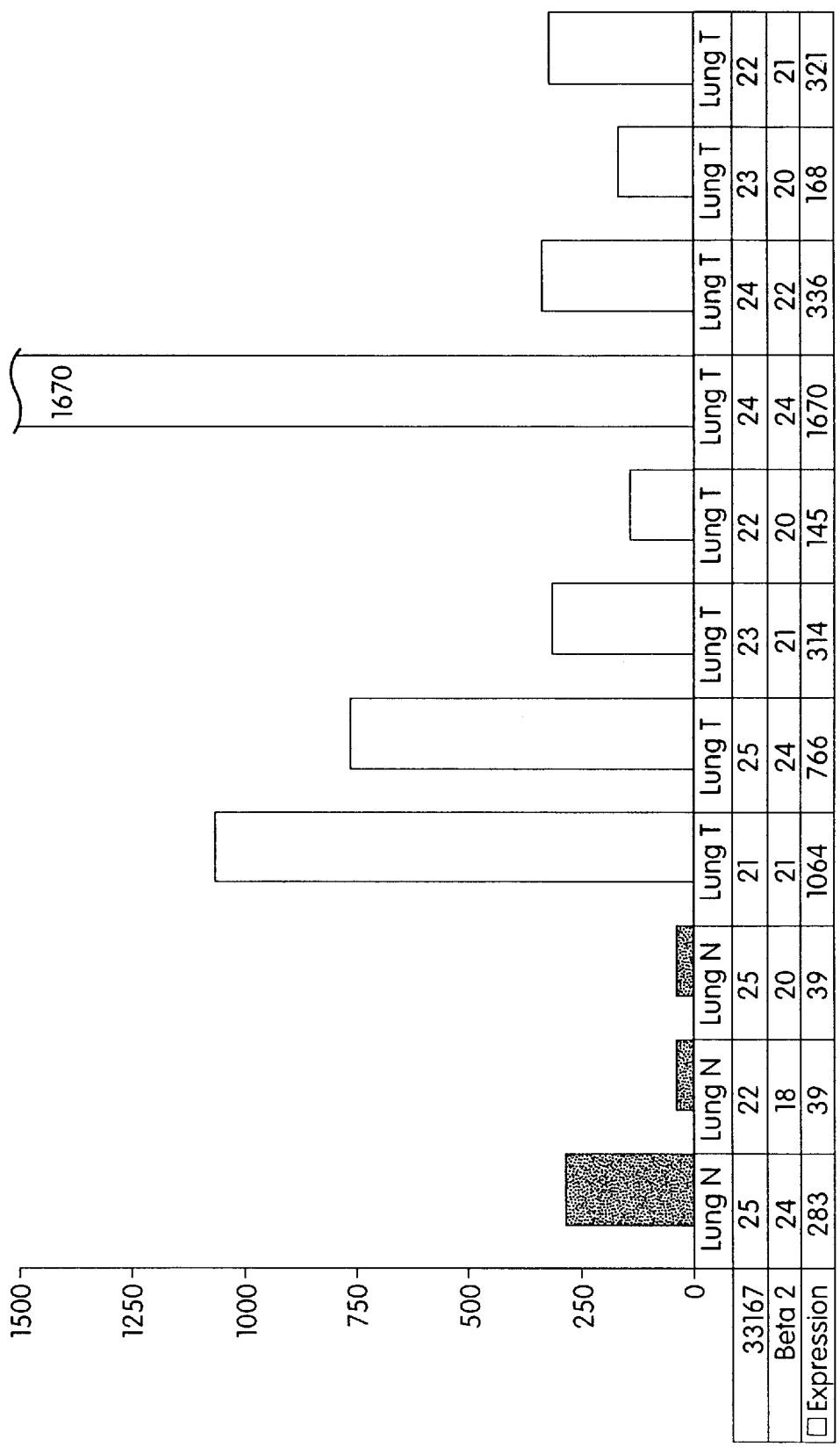
FIG. 8 depicts the results of RT-PCR analyses of HYDL-1 expression normal cells as compared to tumor cells. Panel A is a graph depicting HYDL-1 expression in clinical lung tumors as compared to normal lung; Panel B is a graph depicting HYDL-1 in various tumor cell lines.

The expression of HYDL-1 was determined in transformed cells using PCR analysis. As shown in FIG. 8A, HYDL-1 expression is increased in 6 of 8 clinical lung tumor samples as compared to 3 clinical normal samples. Similarly, in situ hybridization experiments indicated moderate to high expression of HYDL-1 in lung tumor cells (4 of 4), in contrast to no expression in normal lung (0 of 2).

Figure 8B:

PCR analysis was also used to determine HYDL-1 expression in a variety of tumor cell lines. Increased levels of HYDL-1 expression were observed in multiple tumor cell lines, including breast, colon (colorectal), and lung cell lines (see FIG. 8B). In situ hybridization experiments also demonstrated moderate to high levels of HYDL-1 expression in tumor cells of primary colon tumors (3 of 3) compared to normal colon (0 of 2), and in cells of primary breast tumors (3 of 4) as compared to normal breast (1 of 2).

Taken together, these data indicate that increased expression of HYDL-1 may contribute to tumor cell proliferation.

Example 4

Expression of Recombinant HYDL-1 Protein in Bacterial Cells

In this example, human HYDL-1 is expressed as a recombinant glutathione-S-transferase (GST) fusion polypeptide in E. coli and the fusion polypeptide is isolated and characterized. Specifically, HYDL-1 is fused to GST and this fusion polypeptide is expressed in E. coli, e.g., strain PEB199. Expression of the GST-HYDL-1 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant HYDL-1 Potein in COS Cells

To express the human HYDL-1 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire HYDL-1 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the HYDL-1 DNA sequence is amplified by PCR using two primers. The 5' primer contains the restriction site of interest followed by approximately twenty nucleotides of the HYDL-1 coding sequence starting from the initiation codon; the 3' end sequence contains complementary sequences to the other restriction site of interest, a translation stop codon, the HA tag or FLAG tag and the last 20 nucleotides of the HYDL-1 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the HYDL-1 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the HYDL-1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the HYDL-1 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the HYDL-1 coding sequence is cloned directly into the polylinker of the pCDNA/Amp vector using the appropriate restriction sites. The resulting plasmid is transfected into COS cells in the manner described above, and the expression of the HYDL-1 polypeptide is detected by radiolabelling and immunoprecipitation using an HYDL-1 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule selected from the group consisting of:
   (a) a nucleic acid molecule comprising the nucleotide sequence set forth in SEQ ID NO:1, or a complement thereof; and
   (b) a nucleic acid molecule comprising the nucleotide sequence set forth in SEQ ID NO:3, or a complement thereof.

2. An isolated nucleic acid molecule which encodes a polypeptide comprising the amino acid sequence set forth in SEQ ID NO:2, or a complement thereof.

3. An isolated nucleic acid molecule which encodes a naturally occurring allelic variant of a polypeptide comprising the amino acid sequence set forth in SEQ ID NO:2, or a complement thereof.

4. An isolated nucleic acid molecule which hybridizes to the nucleic acid molecule of any one of claims 1, 2, or 3 under stringent conditions.

5. An isolated nucleic acid molecule comprising the nucleic acid molecule of any one of claims 1, 2, or 4 and a nucleotide sequ encoding a heterologous polypeptide.

6. A vector comprising the nucleic acid molecule of any one of claims 1, 2 or 4.

7. The vector of claim 6, which is an expression vector.

8. A host cell transfected with the expression vector of claim 7,

9. A method of producing a polypeptide comprising culturing the host cell of claim 8 in an appropriate culture medium to, thereby, produce the polypeptide.

10. A method for detecting the presence of a nucleic acid molecule of any one of claims 1, 2, or 4 in a sample comprising:
   a) contacting the sample with a nucleic acid probe or primer which selectively hybridizes to the nucleic acid molecule; and
   b) determining whether the nucleic acid probe or primer binds to a nucleic acid molecule in the sample to thereby detect the presence of a nucleic acid molecule of any one of claims 1, 2, or 4 in the sample.

11. The method of claim 10, wherein the sample comprises mRNA molecules and is contacted with a nucleic acid probe.

12. A kit comprising a compound which selectively hybridizes to a nucleic acid molecule of any one of claims 1, 2, or 4 and instructions for use.

* * * * *

UNITED STATES PATENT AND TRADEMARK OFFICE
CERTIFICATE OF CORRECTION

PATENT NO. : 6,500,657 B1
DATED : December 31, 2002
INVENTOR(S) : Glucksmann et al.

It is certified that error appears in the above-identified patent and that said Letters Patent is hereby corrected as shown below:

Column 84,
Line 63, replace "4" with -- 3 --.
Line 64, replace "sequ" with -- sequence --.
Line 66, replace "4" with -- 3 --.

Column 85,
Line 2, replace "," with -- . --.
Line 7, replace "4" with -- 3 --.

Column 86
Line 4, replace "4" with -- 3 --.
Line 9, replace "4" with -- 3 --.

Signed and Sealed this

Twenty-second Day of July, 2003

JAMES E. ROGAN
*Director of the United States Patent and Trademark Office*

SEQUENCE LISTING

<160> NUMBER OF SEQ ID NOS: 11

<210> SEQ ID NO 1
<211> LENGTH: 1332
<212> TYPE: DNA
<213> ORGANISM: Homo sapiens
<220> FEATURE:
<221> NAME/KEY: CDS
<222> LOCATION: (47)..(991)

-continued

```
<400> SEQUENCE: 1
cgagctaggg cgggagaagg agcgcgggga ggacgtacct tgtggg atg cga gcc        55
                                                    Met Arg Ala
                                                    1 ggc caa cag ctt gca agc atg ctc cgc tgg acc cga gcc tgg agg ctc      103
Gly Gln Gln Leu Ala Ser Met Leu Arg Trp Thr Arg Ala Trp Arg Leu
      5                  10                  15 ccg cgt gag gga ctc ggc ccc cac ggc cct agc ttc gcg agg gtg cct      151
Pro Arg Glu Gly Leu Gly Pro His Gly Pro Ser Phe Ala Arg Val Pro
 20                  25                  30                  35 gtc gca ccc agc agc agc agc ggc ggc cga ggg ggc gcc gag ccg agg      199
Val Ala Pro Ser Ser Ser Ser Gly Gly Arg Gly Gly Ala Glu Pro Arg
                 40                  45                  50 ccg ctt ccg ctt tcc tac agg ctt ctg gac ggg gag gca gcc ctc ccg      247
Pro Leu Pro Leu Ser Tyr Arg Leu Leu Asp Gly Glu Ala Ala Leu Pro
             55                  60                  65 gcc gtc gtc ttt ttg cac ggg ctc ttc ggc agc aaa act aac ttc aac      295
Ala Val Val Phe Leu His Gly Leu Phe Gly Ser Lys Thr Asn Phe Asn
         70                  75                  80 tcc atc gcc aag atc ttg gcc cag cag aca ggc cgt agg gtg ctg acg      343
Ser Ile Ala Lys Ile Leu Ala Gln Gln Thr Gly Arg Arg Val Leu Thr
     85                  90                  95 gtg gat gct cgt aac cac ggt gac agc ccc cac agc cca gac atg agc      391
Val Asp Ala Arg Asn His Gly Asp Ser Pro His Ser Pro Asp Met Ser
100                 105                 110                 115 tac gag atc atg agc cag gac ctg cag gac ctt ctg ccc cag ctg ggc      439
Tyr Glu Ile Met Ser Gln Asp Leu Gln Asp Leu Leu Pro Gln Leu Gly
                 120                 125                 130 ctg gtg ccc tgc gtc gtc gtt ggc cac agc atg gga gga aag aca gcc      487
Leu Val Pro Cys Val Val Val Gly His Ser Met Gly Gly Lys Thr Ala
             135                 140                 145 atg ctg ctg gca cta cag agg cca gag ctg gtg gaa cgt ctc att gct      535
Met Leu Leu Ala Leu Gln Arg Pro Glu Leu Val Glu Arg Leu Ile Ala
         150                 155                 160 gta gat atc agc cca gtg gaa agc aca ggt gtc tcc cac ttt gca acc      583
Val Asp Ile Ser Pro Val Glu Ser Thr Gly Val Ser His Phe Ala Thr
     165                 170                 175 tat gtg gca gcc atg agg gcc atc aac atc gca gat gag ctg ccc cgc      631
Tyr Val Ala Ala Met Arg Ala Ile Asn Ile Ala Asp Glu Leu Pro Arg
180                 185                 190                 195 tcc cgt gcc cga aaa ctg gcg gat gaa cag ctc agt tct gtc atc cag      679
Ser Arg Ala Arg Lys Leu Ala Asp Glu Gln Leu Ser Ser Val Ile Gln
                 200                 205                 210 gac atg gcc gtg cgg cag cac ctg ctc act aac ctg gta gag gta gac      727
Asp Met Ala Val Arg Gln His Leu Leu Thr Asn Leu Val Glu Val Asp
             215                 220                 225 ggg cgc ttc gtg tgg agg gtg aac ttg gat gcc ctg acc cag cac cta      775
Gly Arg Phe Val Trp Arg Val Asn Leu Asp Ala Leu Thr Gln His Leu
         230                 235                 240 gac aag atc ttg gct ttc cca cag agg cag gag tcc tac ctc ggg cca      823
Asp Lys Ile Leu Ala Phe Pro Gln Arg Gln Glu Ser Tyr Leu Gly Pro
     245                 250                 255 aca ctc ttt ctc ctt ggt gga aac tcc cag ttc gtg cat ccc agc cac      871
Thr Leu Phe Leu Leu Gly Gly Asn Ser Gln Phe Val His Pro Ser His
260                 265                 270                 275 cac cct gag att atg cgg ctc ttc cct cgg gcc cag atg cag acg gtg      919
His Pro Glu Ile Met Arg Leu Phe Pro Arg Ala Gln Met Gln Thr Val
                 280                 285                 290 ccg aac gct ggc cac tgg atc cac gct gac cgc cca cag gac ttc ata      967
```

```
Pro Asn Ala Gly His Trp Ile His Ala Asp Arg Pro Gln Asp Phe Ile
                295                 300                 305 gct gcc atc cga ggc ttc ctg gtc taagagttgc tgcaagaag atggccggc      1021
Ala Ala Ile Arg Gly Phe Leu Val
            310             315 gtggtggctc atgcctgtaa ttccagcact ttgggaggct aaggcgggag gatgacttga    1081
ggccaggagt tggagaccag cctggccaac atgtgaaac cctgtctcta ctaaaaatac    1141
aaaaattagc ctggcgtggt ggtgcacacc tgtaatccca gctactctgg aggctgaggc    1201
aggagaatca cttgaaccct ggaggcagag gttgcaatga gccgagatca caccactaca    1261
ctccagccta ggcaacagag caagactctg tctcaaaaaa aaaaaaaaaa aaaaaaaaa    1321 aggggccgta g                                                         1332

<210> SEQ ID NO 2
<211> LENGTH: 315
<212> TYPE: PRT
<213> ORGANISM: Homo sapiens

<400> SEQUENCE: 2

Met Arg Ala Gly Gln Gln Leu Ala Ser Met Leu Arg Trp Thr Arg Ala
  1               5                  10                  15

Trp Arg Leu Pro Arg Glu Gly Leu Gly Pro His Gly Pro Ser Phe Ala
                 20                  25                  30

Arg Val Pro Val Ala Pro Ser Ser Ser Gly Gly Arg Gly Gly Ala
             35                  40                  45

Glu Pro Arg Pro Leu Pro Leu Ser Tyr Arg Leu Leu Asp Gly Glu Ala
         50                  55                  60

Ala Leu Pro Ala Val Val Phe Leu His Gly Leu Phe Gly Ser Lys Thr
 65                  70                  75                  80

Asn Phe Asn Ser Ile Ala Lys Ile Leu Ala Gln Gln Thr Gly Arg Arg
                 85                  90                  95

Val Leu Thr Val Asp Ala Arg Asn His Gly Asp Ser His Ser Pro
            100                 105                 110

Asp Met Ser Tyr Glu Ile Met Ser Gln Asp Leu Gln Asp Leu Leu Pro
            115                 120                 125

Gln Leu Gly Leu Val Pro Cys Val Val Gly His Ser Met Gly Gly
        130                 135                 140

Lys Thr Ala Met Leu Leu Ala Leu Gln Arg Pro Glu Leu Val Glu Arg
145                 150                 155                 160

Leu Ile Ala Val Asp Ile Ser Pro Val Glu Ser Thr Gly Val Ser His
                165                 170                 175

Phe Ala Thr Tyr Val Ala Ala Met Arg Ala Ile Asn Ile Ala Asp Glu
            180                 185                 190

Leu Pro Arg Ser Arg Ala Arg Lys Leu Ala Asp Glu Gln Leu Ser Ser
        195                 200                 205

Val Ile Gln Asp Met Ala Val Arg Gln His Leu Leu Thr Asn Leu Val
    210                 215                 220

Glu Val Asp Gly Arg Phe Val Trp Arg Val Asn Leu Asp Ala Leu Thr
225                 230                 235                 240

Gln His Leu Asp Lys Ile Leu Ala Phe Pro Gln Arg Gln Glu Ser Tyr
                245                 250                 255

Leu Gly Pro Thr Leu Phe Leu Leu Gly Gly Asn Ser Gln Phe Val His
            260                 265                 270

Pro Ser His His Pro Glu Ile Met Arg Leu Phe Pro Arg Ala Gln Met
```

-continued

```
                275                 280                 285
Gln Thr Val Pro Asn Ala Gly His Trp Ile His Ala Asp Arg Pro Gln
            290                 295                 300
Asp Phe Ile Ala Ala Ile Arg Gly Phe Leu Val
305                 310                 315

<210> SEQ ID NO 3
<211> LENGTH: 945
<212> TYPE: DNA
<213> ORGANISM: Homo sapiens
<220> FEATURE:
<221> NAME/KEY: CDS
<222> LOCATION: (1)..(945)

<400> SEQUENCE: 3 atg cga gcc ggc caa cag ctt gca agc atg ctc cgc tgg acc cga gcc        48
Met Arg Ala Gly Gln Gln Leu Ala Ser Met Leu Arg Trp Thr Arg Ala
  1               5                  10                  15 tgg agg ctc ccg cgt gag gga ctc ggc ccc cac ggc cct agc ttc gcg        96
Trp Arg Leu Pro Arg Glu Gly Leu Gly Pro His Gly Pro Ser Phe Ala
             20                  25                  30 agg gtg cct gtc gca ccc agc agc agc ggc ggc cga ggg ggc gcc             144
Arg Val Pro Val Ala Pro Ser Ser Ser Gly Gly Arg Gly Gly Ala
         35                  40                  45 gag ccg agg ccg ctt ccg ctt tcc tac agg ctt ctg gac ggg gag gca        192
Glu Pro Arg Pro Leu Pro Leu Ser Tyr Arg Leu Leu Asp Gly Glu Ala
     50                  55                  60 gcc ctc ccg gcc gtc gtc ttt ttg cac ggg ctc ttc ggc agc aaa act        240
Ala Leu Pro Ala Val Val Phe Leu His Gly Leu Phe Gly Ser Lys Thr
 65                  70                  75                  80 aac ttc aac tcc atc gcc aag atc ttg gcc cag cag aca ggc cgt agg        288
Asn Phe Asn Ser Ile Ala Lys Ile Leu Ala Gln Gln Thr Gly Arg Arg
                 85                  90                  95 gtg ctg acg gtg gat gct cgt aac cac ggt gac agc ccc cac agc cca        336
Val Leu Thr Val Asp Ala Arg Asn His Gly Asp Ser Pro His Ser Pro
            100                 105                 110 gac atg agc tac gag atc atg agc cag gac ctg cag gac ctt ctg ccc        384
Asp Met Ser Tyr Glu Ile Met Ser Gln Asp Leu Gln Asp Leu Leu Pro
        115                 120                 125 cag ctg ggc ctg gtg ccc tgc gtc gtc gtt ggc cac agc atg gga gga        432
Gln Leu Gly Leu Val Pro Cys Val Val Val Gly His Ser Met Gly Gly
    130                 135                 140 aag aca gcc atg ctg ctg gca cta cag agg cca gag ctg gtg gaa cgt        480
Lys Thr Ala Met Leu Leu Ala Leu Gln Arg Pro Glu Leu Val Glu Arg
145                 150                 155                 160 ctc att gct gta gat atc agc cca gtg gaa agc aca ggt gtc tcc cac        528
Leu Ile Ala Val Asp Ile Ser Pro Val Glu Ser Thr Gly Val Ser His
                165                 170                 175 ttt gca acc tat gtg gca gcc atg agg gcc atc aac atc gca gat gag        576
Phe Ala Thr Tyr Val Ala Ala Met Arg Ala Ile Asn Ile Ala Asp Glu
            180                 185                 190 ctg ccc cgc tcc cgt gcc cga aaa ctg gcg gat gaa cag ctc agt tct        624
Leu Pro Arg Ser Arg Ala Arg Lys Leu Ala Asp Glu Gln Leu Ser Ser
        195                 200                 205 gtc atc cag gac atg gcc gtg cgg cag cac ctg ctc act aac ctg gta        672
Val Ile Gln Asp Met Ala Val Arg Gln His Leu Leu Thr Asn Leu Val
    210                 215                 220 gag gta gac ggg cgc ttc gtg tgg agg gtg aac ttg gat gcc ctg acc        720
Glu Val Asp Gly Arg Phe Val Trp Arg Val Asn Leu Asp Ala Leu Thr
225                 230                 235                 240
```

-continued

```
cag cac cta gac aag atc ttg gct ttc cca cag agg cag gag tcc tac    768
Gln His Leu Asp Lys Ile Leu Ala Phe Pro Gln Arg Gln Glu Ser Tyr
            245                 250                 255 ctc ggg cca aca ctc ttt ctc ctt ggt gga aac tcc cag ttc gtg cat    816
Leu Gly Pro Thr Leu Phe Leu Leu Gly Gly Asn Ser Gln Phe Val His
        260                 265                 270 ccc agc cac cac cct gag att atg cgg ctc ttc cct cgg gcc cag atg    864
Pro Ser His His Pro Glu Ile Met Arg Leu Phe Pro Arg Ala Gln Met
    275                 280                 285 cag acg gtg ccg aac gct ggc cac tgg atc cac gct gac cgc cca cag    912
Gln Thr Val Pro Asn Ala Gly His Trp Ile His Ala Asp Arg Pro Gln
290                 295                 300 gac ttc ata gct gcc atc cga ggc ttc ctg gtc                        945
Asp Phe Ile Ala Ala Ile Arg Gly Phe Leu Val
305                 310                 315

<210> SEQ ID NO 4
<211> LENGTH: 287
<212> TYPE: PRT
<213> ORGANISM: Haemophilus influenzae

<400> SEQUENCE: 4

Met Ile Phe Ile Phe Ile Ser Leu Phe Ala Lys Ile Phe Phe Asn Tyr
 1               5                  10                  15

Asn Asp Phe Phe Thr Asn Ser His Val Lys Ile Met Ala Lys Ser Leu
            20                  25                  30

Leu Asn Tyr Gln Phe His Gln Val Lys Gln Thr Ile Asn Thr Pro Val
        35                  40                  45

Leu Ile Phe Ile His Gly Leu Phe Gly Asp Met Asp Asn Leu Gly Val
    50                  55                  60

Ile Ala Arg Ala Phe Ser Glu His Tyr Ser Ile Leu Arg Ile Asp Leu
65                  70                  75                  80

Arg Asn His Gly His Ser Phe His Ser Glu Lys Met Asn Tyr Gln Leu
                85                  90                  95

Met Ala Glu Asp Val Ile Ala Val Ile Arg His Leu Asn Leu Ser Lys
            100                 105                 110

Val Ile Leu Ile Gly His Ser Met Gly Gly Lys Thr Ala Met Lys Ile
        115                 120                 125

Thr Ala Leu Cys Pro Glu Leu Val Glu Lys Leu Ile Val Ile Asp Met
    130                 135                 140

Ser Pro Met Pro Tyr Glu Gly Phe Gly His Lys Asp Val Phe Asn Gly
145                 150                 155                 160

Leu Phe Ala Val Lys Asn Ala Lys Pro Glu Asn Arg Gln Gln Ala Lys
                165                 170                 175

Pro Ile Leu Lys Gln Glu Ile Asn Asp Glu Asp Val Val Gln Phe Met
            180                 185                 190

Leu Lys Ser Phe Asp Val Asn Ser Ala Asp Cys Phe Arg Phe Asn Leu
        195                 200                 205

Thr Ala Leu Phe Asn Asn Tyr Ala Asn Ile Met Asp Trp Glu Lys Val
    210                 215                 220

Arg Val Phe Thr Pro Thr Leu Phe Ile Lys Gly Gly Asn Ser Ser Tyr
225                 230                 235                 240

Ile Lys Ile Glu Asn Ser Glu Lys Ile Leu Glu Gln Phe Pro Asn Ala
                245                 250                 255

Thr Ala Phe Thr Ile Asn Gly Ser Gly His Trp Val His Ala Glu Lys
            260                 265                 270
```

```
Pro Asp Phe Val Ile Arg Ala Ile Lys Arg Phe Leu Asn Lys Asn
        275                 280                 285
```

<210> SEQ ID NO 5
<211> LENGTH: 254
<212> TYPE: PRT
<213> ORGANISM: Escherichia coli

<400> SEQUENCE: 5

```
Met Lys Leu Asn Ile Arg Ala Gln Thr Ala Gln Asn Gln His Asn Asn
 1               5                  10                  15

Ser Pro Ile Val Leu Val His Gly Leu Phe Gly Ser Leu Asp Asn Leu
                20                  25                  30

Gly Val Leu Ala Arg Asp Leu Val Asn Asp His Asn Ile Ile Gln Val
                35                  40                  45

Asp Met Arg Asn His Gly Leu Ser Pro Arg Asp Pro Val Met Asn Tyr
        50                  55                  60

Pro Ala Met Ala Gln Asp Leu Val Asp Thr Leu Asp Ala Gln Gln Ile
 65                  70                  75                  80

Asp Lys Ala Thr Phe Ile Gly His Ser Met Gly Gly Lys Ala Val Met
                85                  90                  95

Ala Leu Thr Ala Leu Ala Ser Asp Arg Ile Asp Lys Leu Val Ala Ile
                100                 105                 110

Asp Ile Ala Pro Val Asp Tyr His Val Arg Arg His Asp Glu Ile Phe
                115                 120                 125

Ala Ala Ile Asn Ala Val Ser Glu Ser Asp Ala Gln Thr Arg Gln Gln
        130                 135                 140

Ala Ala Ala Ile Met Arg Gln His Leu Asn Glu Glu Gly Val Ile Gln
145                 150                 155                 160

Phe Leu Leu Lys Ser Phe Val Asp Gly Glu Trp Arg Phe Asn Val Pro
                165                 170                 175

Val Leu Trp Asp Gln Tyr Pro His Ile Val Gly Trp Glu Lys Ile Pro
                180                 185                 190

Ala Trp Asp His Pro Ala Leu Phe Ile Pro Gly Gly Asn Ser Pro Tyr
                195                 200                 205

Val Ser Glu Gln Tyr Arg Asp Asp Leu Leu Ala Gln Phe Pro Gln Ala
        210                 215                 220

Arg Ala His Val Ile Ala Gly Ala Gly His Trp Val His Ala Glu Lys
225                 230                 235                 240

Pro Asp Ala Val Leu Arg Ala Ile Arg Arg Tyr Leu Asn Asp
                245                 250
```

<210> SEQ ID NO 6
<211> LENGTH: 299
<212> TYPE: PRT
<213> ORGANISM: Caenorhabditis elegans

<400> SEQUENCE: 6

```
Met Leu Val Ser Arg Asn Leu Ala Lys Thr Ile Ser Asn Ser Lys Asn
 1               5                  10                  15

Ala Lys Asn Ile His Thr Ser Cys Arg Lys Phe Ala Pro Val Pro Met
                20                  25                  30

Thr Tyr Ala Ser Tyr Ser Ser Pro Glu Leu Asp Arg Asn Ser Pro Leu
                35                  40                  45

Val Ile Val His Gly Leu Phe Gly Gln Lys Gln Asn Trp Asn Ser Val
                50                  55                  60
```

Gly Lys Ala Leu His Lys Leu Glu Ala Pro Val Tyr Ala Val Asp
 65                  70                  75                  80

Val Arg Asn His Gly Ser Ser Pro His Thr Glu Thr Met Ser Tyr Thr
                 85                  90                  95

Glu Met Ala Glu Asp Leu Val Leu Phe Ile Asp Lys Val Lys Glu Glu
            100                 105                 110

Thr Lys Lys Thr Arg Val Asn Leu Leu Gly His Ser Met Gly Gly Lys
        115                 120                 125

Ile Val Met Arg Leu Ala Ile Asp Ser Lys Trp Ser Asp Arg Ile Glu
130                 135                 140

Lys Leu Ile Val Glu Asp Val Ser Pro Lys Gly Tyr Ser Arg Arg His
145                 150                 155                 160

Leu Glu Phe Arg Glu Leu Ile Lys Thr Met Arg Asn Val Asp Leu Cys
                165                 170                 175

Arg Thr Arg Lys Glu Ile Leu Lys Asp Leu Glu Ser Ala Ile Pro Asp
            180                 185                 190

Leu Ala Met Arg Gln Phe Ile Leu Thr Asn Leu Gln Pro Ser Ser Glu
        195                 200                 205

Asn Glu Gly Gln Met Glu Trp Lys Ile Asn Ile Asn Thr Ile Asp Ser
210                 215                 220

His Val Asp Glu Ile Leu Gly Tyr Thr Leu Pro Val Gly Ser Phe Arg
225                 230                 235                 240

Gly Pro Thr Leu Phe Leu His Gly Ala Asn Ser Gly Tyr Val Pro Asp
                245                 250                 255

Asp His Lys Pro Asp Ile Lys Cys Leu Phe Pro Gln Val Gln Phe Asp
            260                 265                 270

Ala Ile Pro Asp Ser Gly His Trp Val His Ala Glu Lys Pro Gln Leu
        275                 280                 285

Phe Ile Asn Ser Val Tyr Lys Phe Leu Lys Pro
        290                 295

<210> SEQ ID NO 7
<211> LENGTH: 297
<212> TYPE: PRT
<213> ORGANISM: Caenorhabditis elegans

<400> SEQUENCE: 7

Met Asn Ser Lys Leu Leu Asn Leu Ala Arg Arg Phe Pro His Ser Asp
  1               5                  10                  15

Ser Thr Ser Ser Met Met Leu Ala Asn Leu Thr Phe Gly Asn Met Arg
                 20                  25                  30

Ser Lys Gly Thr Pro Leu Ile Leu Val Pro Gly Leu Phe Gly Thr Lys
            35                  40                  45

Glu Asn Trp Ile Gln Val Gly Lys Asp Leu Ser Gln Arg Leu Gly Cys
        50                  55                  60

Met Val Phe Ala Val Glu Asn Arg Asn His Gly Ser Phe Ser Lys Ala
 65                  70                  75                  80

Ala Ser Met Thr Tyr Glu Glu Met Ala Asp Leu Val Gly Phe Ile
                 85                  90                  95

Asp Trp Val Arg Lys Ile Thr Gly Glu Asp Lys Val Asn Leu His Gly
            100                 105                 110

His Ser Met Gly Gly Lys Ala Val Thr Gln Leu Ala Thr Thr Pro Glu
        115                 120                 125

Tyr Ser Ser Arg Ile Lys Ser Leu Ile Val Glu Asp Met Ser Pro Leu
        130                 135                 140

```
Gly Tyr Pro Leu Lys Arg Ala Glu Tyr Leu Glu Cys Ile Lys Gln Met
145                 150                 155                 160

Ile Ala Thr Asp Met Asn Lys Ser Arg Ser Glu Val Met Ala Glu Leu
                165                 170                 175

Gly Glu Lys Val Ser Lys Val Leu Leu Tyr Gln Phe Val Arg Gly Asn
            180                 185                 190

Leu Gly Glu Asp Val Asn Gly Lys Ala His Trp Ile Cys Asn Leu Asn
        195                 200                 205

Val Ile Asp Glu Thr Tyr Ile Tyr Leu Leu Ser His Asp Ile Arg Phe
    210                 215                 220

Gly Val Phe Asp Gly Pro Thr Leu Phe Gln Arg Ala Pro Gly Ser Gly
225                 230                 235                 240

Phe Leu Pro Ala Ala His Lys Asn Arg Val Glu Lys Met Phe Pro Met
                245                 250                 255

Val Gln Phe Ala Glu Thr Ala Trp Ser Asn His Trp Ile His Ala Asp
            260                 265                 270

Asp Pro Lys Phe Phe Val Asp Ser Ile Cys Glu Phe Leu Glu Glu Pro
        275                 280                 285

Asp Gln Leu Gly Met Arg Ala Tyr Ile
    290                 295

<210> SEQ ID NO 8
<211> LENGTH: 308
<212> TYPE: PRT
<213> ORGANISM: Drosophila melanogaster

<400> SEQUENCE: 8

Met Gln Arg Leu Thr Lys Ser Leu Arg Ser Leu Pro Phe Pro Ala Gly
1               5                   10                  15

Lys Ile Leu Arg Thr Gln Leu Val Val Arg Arg Glu Tyr Ser Ser Glu
            20                  25                  30

Ile Pro Asp Pro Val Glu Leu Ser Phe Asp Ser Tyr Thr Gly Glu Asn
        35                  40                  45

Pro Glu Thr Ser Pro Pro Leu Leu Thr Tyr His Gly Leu Phe Gly Ser
    50                  55                  60

Lys Gln Asn Trp Arg Gly Ile Ser Lys Ala Leu Val Arg Lys Val Ser
65                  70                  75                  80

Arg Lys Val Tyr Ala Ile Asp Val Arg Asn His Gly Glu Ser Pro His
                85                  90                  95

Ser Ser Val His Asn Ser Lys Ala Met Ser Glu Asp Leu Arg Leu Phe
            100                 105                 110

Met Glu Gln Arg Ser His Pro Asn Ala Ala Cys Met Gly His Ser Met
        115                 120                 125

Gly Gly Arg Ser Met Met Tyr Phe Ala Arg Lys Tyr Pro Glu Leu Val
    130                 135                 140

Glu Arg Leu Ile Val Val Asp Ile Ser Pro Ile Ser Val Pro Arg Ser
145                 150                 155                 160

Thr Gly Glu Met Thr Glu Ile Phe Asp Ala Met Val Ser Leu Asp Leu
                165                 170                 175

Ser Pro Ser Met Ser Met Ser Glu Gly Arg Lys Ile Ala Arg Glu Lys
            180                 185                 190

Leu Leu Lys Ala Thr Glu Asp Glu Thr Val Asp Phe Ile Met Leu Asn
        195                 200                 205

Leu Arg Lys Asn Pro Asp Thr Gly Ala Phe Ser Trp Ala Cys Asn Ala
```

-continued

```
                    210                 215                 220
His Val Leu Arg Glu Phe Leu Thr Arg Phe Asp Lys Tyr Gln Ser Asn
225                 230                 235                 240

Leu Glu Glu Leu Pro Pro Tyr Thr Gly Pro Thr Thr Phe Ile Cys Gly
                    245                 250                 255

Thr Arg Ser Pro Tyr Met Arg Arg Glu Gln Trp Pro Gln Ile Gln Lys
                260                 265                 270

Met Phe Pro Asn Ser Glu Ile His Trp Leu Asp Ala Gly His Leu Val
            275                 280                 285

His Phe Glu Lys Pro Gln Glu Phe Leu Thr Ile Val Ser Glu Phe Leu
290                 295                 300

Asn Arg Thr Glu
305

<210> SEQ ID NO 9
<211> LENGTH: 270
<212> TYPE: PRT
<213> ORGANISM: Schizosaccharomyces pombe

<400> SEQUENCE: 9

Met Ser Leu Lys Pro Val Lys Leu Ala Phe Glu Lys Tyr Ser Ala Thr
1               5                   10                  15

Val Ala Lys His Pro Pro Val Leu Ile Phe His Gly Leu Leu Gly Ser
                20                  25                  30

Lys Arg Asn Trp Arg Ser Leu Ala Lys Lys Phe Ser Cys Lys Leu Asp
            35                  40                  45

Arg Asp Ile Tyr Ala Ile Asp Gln Arg Cys His Gly Asp Ser Pro Cys
        50                  55                  60

Val Ala Pro Leu Ser Tyr Ser Ala Met Ala Leu Asp Ala Phe Gln Phe
65                  70                  75                  80

Met Lys Asp His Lys Leu Asp Lys Ala Ser Ile Ile Gly His Ser Met
                85                  90                  95

Gly Ala Lys Thr Ala Met Val Thr Ala Leu Lys Trp Pro Asp Lys Val
            100                 105                 110

Glu Lys Leu Val Val Val Asp Asn Ser Pro Trp Tyr Gln Asp Leu Pro
        115                 120                 125

Arg Asp Tyr Gly Ala Tyr Phe Arg Lys Met Ile Gln Ile Asp Glu Ala
    130                 135                 140

Asn Ile Thr Lys Tyr Ser Glu Ala Asp Lys Met Met Ser Thr Val Glu
145                 150                 155                 160

Lys Asp Ile Leu Val Arg Ser Phe Leu Leu Ser Asn Leu Lys Lys Asp
                165                 170                 175

Ser Asn Asn Ser Asn Thr Phe Lys Phe Arg Val Pro Ile Glu Leu Ile
            180                 185                 190

Ser Lys Ser Leu Lys Thr Ile Glu Gly Phe Pro Ala Ser Leu Asn Asp
        195                 200                 205

Leu Val Tyr Asp Ser Pro Thr Leu Val Ile Arg Ala Leu Lys Ala Pro
    210                 215                 220

Phe Ile Pro Asp Ser Ala Leu Pro Val Phe Lys Lys Phe Phe Pro Lys
225                 230                 235                 240

Tyr Glu Leu Val Ser Leu Asp Cys Gly His Trp Val His Phe Glu Lys
                245                 250                 255

Pro Lys Glu Phe Ser Glu Ser Ile Ile Asn Phe Leu Asn Asn
            260                 265                 270
```

```
<210> SEQ ID NO 10
<211> LENGTH: 342
<212> TYPE: PRT
<213> ORGANISM: Saccharomyces cerevisiae

<400> SEQUENCE: 10

Met Met Ile Leu Gly Lys Ala Gly Ile Leu Ala Gln Tyr Gly Thr Ile
 1               5                  10                  15

Tyr Val Arg Gln Asn Thr Ile Arg Asn Asn Leu Ser Ser Cys Ile Phe
            20                  25                  30

Lys Gln Ser Leu Cys Ala Phe His Ser Leu Ala Lys Val Leu Gln Gln
        35                  40                  45

Lys Gln Val Pro Leu Asp Leu Ser Tyr Asp Ile Ile Lys Arg Asp Ala
    50                  55                  60

Val Lys Thr Gly Asp Glu Gly Lys Pro Arg Pro Ile Ile Ile Leu
65                  70                  75                  80

His Gly Leu Phe Gly Asn Lys Leu Asn Asn Arg Ser Ile Gly Arg Asn
                85                  90                  95

Leu Asn Lys Lys Leu Gly Arg Asp Val Tyr Leu Leu Asp Leu Arg Asn
            100                 105                 110

His Gly Ser Ser Pro His Ser Ser Val His Asn Tyr Glu Val Met Ser
        115                 120                 125

Glu Asp Val Lys His Phe Ile Thr Lys His Glu Leu Asn Thr Asn Gly
    130                 135                 140

Gly Pro Ile Ile Ile Gly His Ser Met Gly Gly Lys Val Ala Met Met
145                 150                 155                 160

Leu Val Leu Lys Asn Pro Gln Leu Cys Ser Met Leu Val Cys Ile Glu
                165                 170                 175

Asn Ala Pro Val Ser Leu Arg Pro Asn Ala Glu Phe Val Glu Tyr Ile
            180                 185                 190

Lys Ala Leu Met Glu Ile Val Asn Asp Lys Gly Lys Thr Ile Arg Thr
        195                 200                 205

Leu Lys Gln Ala Asp Glu His Leu Ala Glu Arg Ile Gly Gly Asn Glu
    210                 215                 220

Leu Val Arg Arg Phe Leu Leu Thr Ala Leu Lys Lys Val Lys Met Asp
225                 230                 235                 240

Asn Ser Ser Val Ser Ser Tyr Thr Phe Glu Glu Arg Ile Pro Leu
                245                 250                 255

Ala Thr Leu Lys Asp Ala Ile Val Lys Gly Glu Ile Ala Ala Trp Pro
            260                 265                 270

Leu Asp Pro Ala Arg Glu Arg Trp Thr Arg Pro Ala Leu Phe Ile Arg
        275                 280                 285

Ala Thr Gln Ser His Tyr Val Val Asp Glu Tyr Leu Pro Ile Ile Gly
    290                 295                 300

Ala Phe Phe Pro Arg Phe Glu Thr Arg Asp Ile Asp Ala Gly His Trp
305                 310                 315                 320

Val Asn Ala Glu Lys Pro Gly Glu Cys Ala Ser Ile Val Asp Phe
                325                 330                 335

Val Glu Arg His Glu Asp
            340

<210> SEQ ID NO 11
<211> LENGTH: 306
<212> TYPE: PRT
<213> ORGANISM: Drosophila melanogaster
```

-continued

```
<400> SEQUENCE: 11

Met Ala Arg Gln Arg Leu Leu Gly Ser Ile Leu Ser Lys Gly Gly Ala
  1               5                  10                  15

Gln Val Leu Arg Asn Phe Gln Ser Phe Val Gln Gly Thr Arg Leu Glu
             20                  25                  30

Tyr Val Ser Tyr Thr Ser Pro Arg Asn Gln Met Gln Ala Pro Pro Ile
         35                  40                  45

Val Val Met His Asp Leu Asn Leu Ser Leu Glu Ser Trp Arg Gln Val
     50                  55                  60

Ala Val Asn Leu Ser Gln Val Gly Leu Arg Gln Val Ile Thr Val Asp
 65                  70                  75                  80

Ala Arg Asn His Gly Leu Ser Pro Tyr Ile Thr Gly His Ser Pro Met
                 85                  90                  95

His Leu Ala Ala Asp Val Glu Ala Leu Met Ser His Gln Arg Leu Asn
                100                 105                 110

Lys Ile Val Ala Leu Gly His Gly Met Gly Gly Arg Ala Met Met Thr
            115                 120                 125

Leu Ala Leu Thr Gln Pro Gln Leu Val Glu Arg Val Ile Leu Val Asp
    130                 135                 140

Ile Thr Pro Ala Pro Val Pro Ser Asn Phe Tyr Leu Thr Arg Gln Val
145                 150                 155                 160

Phe Glu Met Met Leu Gln Val Ala Pro Ser Ile Pro Ser Asn Leu Ser
                165                 170                 175

Leu Ser Glu Gly Arg Thr Phe Ile Leu Pro Leu Phe Gln Asp Val Val
            180                 185                 190

His Asp Ala Ser Glu Leu Arg Arg Ile Ile Tyr Asn Leu Arg Lys Met
            195                 200                 205

Gln Asp Asn Thr Phe Gly Trp Ala Val Asn Pro Gln Ala Val Leu Ser
    210                 215                 220

Ser Trp Gly Glu Met Met Ile Asn Tyr Glu Ala Thr Leu Gly Gly Leu
225                 230                 235                 240

Arg Pro Tyr Met Gly Glu Val Leu Leu Ile Ala Gly Ser Gln Ser Glu
                245                 250                 255

Phe Val Thr Thr Thr Ser Ile Ala Val Met Gln Arg Tyr Phe Pro Asn
                260                 265                 270

Thr Val Val Gln Ile Leu Asp Ala Gly His Cys Val Tyr Glu Asp Gln
            275                 280                 285

Pro Glu Gln Phe Val Glu Leu Val Val Glu Phe Thr Gln Thr Cys Leu
    290                 295                 300

Val Cys
305
```